United States Patent
Takahashi et al.

(10) Patent No.: US 12,285,184 B2
(45) Date of Patent: Apr. 29, 2025

(54) SURGICAL SYSTEM AND METHOD OF CONTROLLING SURGICAL SYSTEM

(71) Applicant: KAWASAKI JUKOGYO KABUSHIKI KAISHA, Kobe (JP)

(72) Inventors: Kaoru Takahashi, Kobe (JP); Hiroaki Ihara, Kobe (JP); Ayataka Kobayashi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 449 days.

(21) Appl. No.: 17/752,622

(22) Filed: May 24, 2022

(65) Prior Publication Data

US 2022/0378455 A1 Dec. 1, 2022

(30) Foreign Application Priority Data

May 25, 2021 (JP) .................................. 2021-087896

(51) Int. Cl.
*A61B 17/29* (2006.01)
*A61B 34/30* (2016.01)
*A61B 17/00* (2006.01)

(52) U.S. Cl.
CPC .......... *A61B 17/29* (2013.01); *A61B 17/2909* (2013.01); *A61B 2017/00398* (2013.01); *A61B 2017/2903* (2013.01); *A61B 2017/2905* (2013.01); *A61B 2017/2932* (2013.01)

(58) Field of Classification Search
CPC ......... A61B 34/30–34/37; A61B 34/70; A61B 34/71; A61B 17/29–295; A61B 90/10; A61B 90/11; A61B 90/57
See application file for complete search history.

(56) References Cited

U.S. PATENT DOCUMENTS

| | | |
|---|---|---|
| 6,594,552 B1 | 7/2003 | Nowlin et al. |
| 6,879,880 B2 | 4/2005 | Nowlin et al. |
| 7,373,219 B2 | 5/2008 | Nowlin et al. |
| 7,386,365 B2 | 6/2008 | Nixon |
| 7,778,733 B2 | 8/2010 | Nowlin et al. |
| 8,452,447 B2 | 5/2013 | Nixon |
| 8,761,930 B2 | 6/2014 | Nixon |
| 9,002,518 B2 | 4/2015 | Manzo et al. |
| 9,014,856 B2 | 4/2015 | Manzo et al. |

(Continued)

*Primary Examiner* — Kathleen S Holwerda
(74) *Attorney, Agent, or Firm* — METROLEX IP LAW GROUP, PLLC; Robert L. Scott, Esq.

(57) ABSTRACT

A surgical system according to an embodiment may include a patient-side apparatus, an operator-side apparatus including an operation part to receive an operation for operating a surgical instrument attached to an arm of the patient-side apparatus, and a controller configured to control an operation of the surgical instrument based on the operation received by the operation part. The controller is configured to: control rotation amounts of first and second drive parts to drive first and second elongate elements for opening and closing first and second jaw members of the surgical instrument such that an opening angle between the first and second jaw members correspond to an operating angle received by the operation part; and correct, according to a rotation angle of a shaft of the surgical instrument about a rotation axis of the shaft, the rotation amounts of the first and second drive parts that correspond to the operating angle.

20 Claims, 18 Drawing Sheets

(56) References Cited

U.S. PATENT DOCUMENTS

| | | |
|---|---|---|
| 9,085,083 B2 | 7/2015 | Nixon |
| 9,317,651 B2 | 4/2016 | Nixon |
| 9,623,563 B2 | 4/2017 | Nixon |
| 9,872,737 B2 | 1/2018 | Nixon |
| 10,483,881 B2 | 11/2019 | Liao et al. |
| 10,595,946 B2 | 3/2020 | Nixon |
| 10,758,313 B2 * | 9/2020 | Bernstein |
| 2018/0161052 A1 * | 6/2018 | Weir .................. A61B 34/00 |

* cited by examiner

SURGICAL SYSTEM AND METHOD OF CONTROLLING SURGICAL SYSTEM

CROSS REFERENCE TO RELATED APPLICATIONS

This application claims priority based on 35 USC 119 from prior Japanese Patent Application No. 2021-087896 filed on May 25, 2021, entitled "SURGICAL SYSTEM AND METHOD OF CONTROLLING SURGICAL SYSTEM", the entire contents of which are incorporated herein by reference.

BACKGROUND

The disclosure may relate to a surgical system and a method of controlling a surgical system, and particularly relate to a surgical system and a method of controlling a surgical system that are capable of controlling an operation of a surgical instrument based on an instruction from an operation part.

In a related art, there has been known a robotic surgical system including a robot arm, a tool serving as a surgical instrument connected to a distal end of the robot arm, and an input handle serving as an operation part. For example, Patent Document 1 (U.S. Pat. No. 6,594,552) discloses a robotic surgical system configured to perform torque control in an operation of a surgical instrument based on operation received by an operation part. Specifically, the surgical instrument is configured to be operated with four degrees of freedom by four motors in a surgical instrument mounting portion provided at a robot arm. The surgical instrument includes a shaft, two jaw members that are provided at a distal end of the shaft and configured to be opened and closed with each other, and four rotation members (four driven members) configured to be rotated by the four motors provided at a proximal end side of the shaft. Note that the motors are provided in the surgical instrument mounting portion of the robot arm. Two of the rotation members are connected to the two jaw members via cables passing through an inside of the shaft. The robotic surgical system performs torque control to operate the jaw members by rotating the rotation members until the torque applied to the motor reaches a predetermined torque. In the robotic surgical system disclosed in Patent Document 1, three such robot arms are provided at a patient-side cart.

Patent Document 1: U.S. Pat. No. 6,594,552

SUMMARY

In a related art, it may be preferable to reduce the size of the patient-side cart of the robotic surgical system, in particular, to reduce the size of the robot arm which is located around a surgical field so as to secure a work area of an assistant doctor or the like during the surgery. In order to reduce the size of the robot arm around the surgical field, it may be effective to reduce the size of the four motors arranged in the surgical instrument mounting portion. In order to reduce the size of each of the motors, it may be effective to use a speed reducer having a reduction ratio higher than that of a conventional speed reducer so that the downsized motor smaller than a conventional motor can be used to operate the surgical instrument. However, in a case of the robot surgical system described in Patent Document 1 performing torque control of the motor that operates the surgical instrument, if such a speed reducer having the reduction ratio higher than that of the conventional speed reducer is used, a change in a torque of the motor or a current value corresponding to the torque is less likely to be reflected to the behavior of members provided at a distal end side of the surgical instrument. Accordingly, it may be difficult to detect the behavior of the members provided at the distal end side of the surgical instrument by monitoring the change in the torque of the motor or the current value corresponding to the torque of the motor.

In order to solve this problem, it may be effective to control a rotation angle of the motor to operate the surgical instrument, instead of controlling the torque of the motor that drives the surgical instrument. That is, in order to solve this problem, it may be effective to control a rotation angle of the rotation member of the surgical instrument to operate the surgical instrument. In a case where the two jaw members, which are members of the end effector of the surgical instrument, are scissors, a shearing force is generated between the two jaw members when an opening angle between the two jaw members becomes a predetermined angle by further rotating the motors by predetermined rotation angles after the two jaw members are closed. In a case where the two jaw members, which are members of the end effector of the surgical instrument, are graspers, a gripping force is generated between the two jaw members when the opening angle between the two jaw members becomes a predetermined angle by further rotating the motors by predetermined rotation angles after the two jaw members are closed.

However, when the surgical instrument is operated by such control, path lengths of elongate elements consisting of cables in the shaft between the jaw members and the rotation members changes due to the rotation of the shaft. Due to the changes of the path lengths of the elongate elements, the opening angle between the two jaw members may not be controlled to the desired opening angle, which may change the shearing force in the case of the scissors and the gripping force in the case of the graspers.

An object of an embodiment of the disclosure may be to provide a surgical system and a method of controlling a surgical system that are capable of suppressing a change in force generated between two jaw members even when path lengths of elongate elements change.

A first aspect of the disclosure may be a surgical system that may include: a patient-side apparatus including an arm to which a surgical instrument is to be attached; and an operator-side apparatus including an operation part configured to receive an operation for operating the surgical instrument; and a controller configured to control an operation of the surgical instrument based on a command from the operation part, wherein the surgical instrument includes: a shaft; a first jaw member and a second jaw member provided on a side of a distal end of the shaft; a first elongate element for operating the first jaw member; and a second elongate element for operating the second jaw member; wherein the arm includes a first drive part configured to drive the first elongate element and a second drive part configured to drive the second elongate element. The controller is configured to: control rotation amounts of the first drive part and the second drive part such that an opening angle between the first jaw member and the second jaw member corresponds to an operating angle received by the operation part for opening and closing the first jaw member and the second jaw member; and correct, according to a rotation angle of the shaft about a rotation axis of the shaft, the rotation amounts of the first drive part and the second drive part that correspond to the operating angle.

According to the surgical system of the first aspect described above, the controller is configured to control rotation amounts of the first drive part and the second drive part such that the opening angle between the first jaw member and the second jaw member corresponds to the operating angle received by the operation part and the controller is configured to correct the rotation amounts of the first drive part and the second drive part according to the rotation angle of the shaft about the rotation axis of the shaft. With this configuration, even when the path lengths of the first elongate element and the second elongate element are changed due to the rotation of the shaft, the control unit corrects the rotation amounts of the first and second drive parts configured to drive the first and second jaw members, so that the opening angle between the first and second jaw members becomes the desired opening angle. Therefore, even when the path lengths of the first elongate element and the second elongate element change, it is possible to reduce the change in the force generated between the first jaw member and the second jaw member.

A second aspect of the disclosure may be a method of controlling a surgical system, wherein the surgical system includes: a patient-side apparatus including an arm to which a surgical instrument is to be attached; an operator-side apparatus including an operation part configured to receive an operation for operating the surgical instrument; and the controller configured to control an operation of the surgical instrument based on a command from the operation part, wherein the surgical instrument includes: a shaft; a first jaw member and a second jaw member provided on a side of a distal end of the shaft; a first elongate element for operating the first jaw member; and a second elongate element for operating the second jaw member, the arm includes a first drive part configured to drive the first elongate element and a second drive part configured to drive the second elongate element, and the controller is configured to control rotation amounts of the first drive part and the second drive part such that an opening angle between the first jaw member and the second jaw member corresponds to an operating angle received by the operation part for opening and closing the first jaw member and the second jaw member. The method according to the second aspect may include: receiving, from the operation part, the operating angle for opening and closing the first jaw member and the second jaw member; and correcting, according to a rotation angle of the shaft about a rotation axis of the shaft, the rotation amounts of the first drive part and the second drive part that correspond to the operating angle.

That is, the surgical system control method of the second aspect includes correcting, according to the rotation angle of the shaft about the rotation axis of the shaft, the rotation amounts of the first drive part and the second drive part that correspond to the operating angle. With this configuration, even when the path lengths of the first elongate element and the second elongate element are changed due to the rotation of the shaft, the control unit corrects the rotation amounts of the first and second drive parts configured to drive the first and second jaw members, so that the opening angle between the first and second jaw members becomes the desired opening angle. Therefore, it is possible to provide a surgical system control method that can suppress the change in the force generated between the first jaw member and the second jaw member. even when the path lengths of the first elongate element and the second elongate element change.

According to at least one of the aspects described above, even when the path length of the elongate element changes, the change in force due to the two jaw members can be reduced.

DETAILED DESCRIPTION

Figure 1:
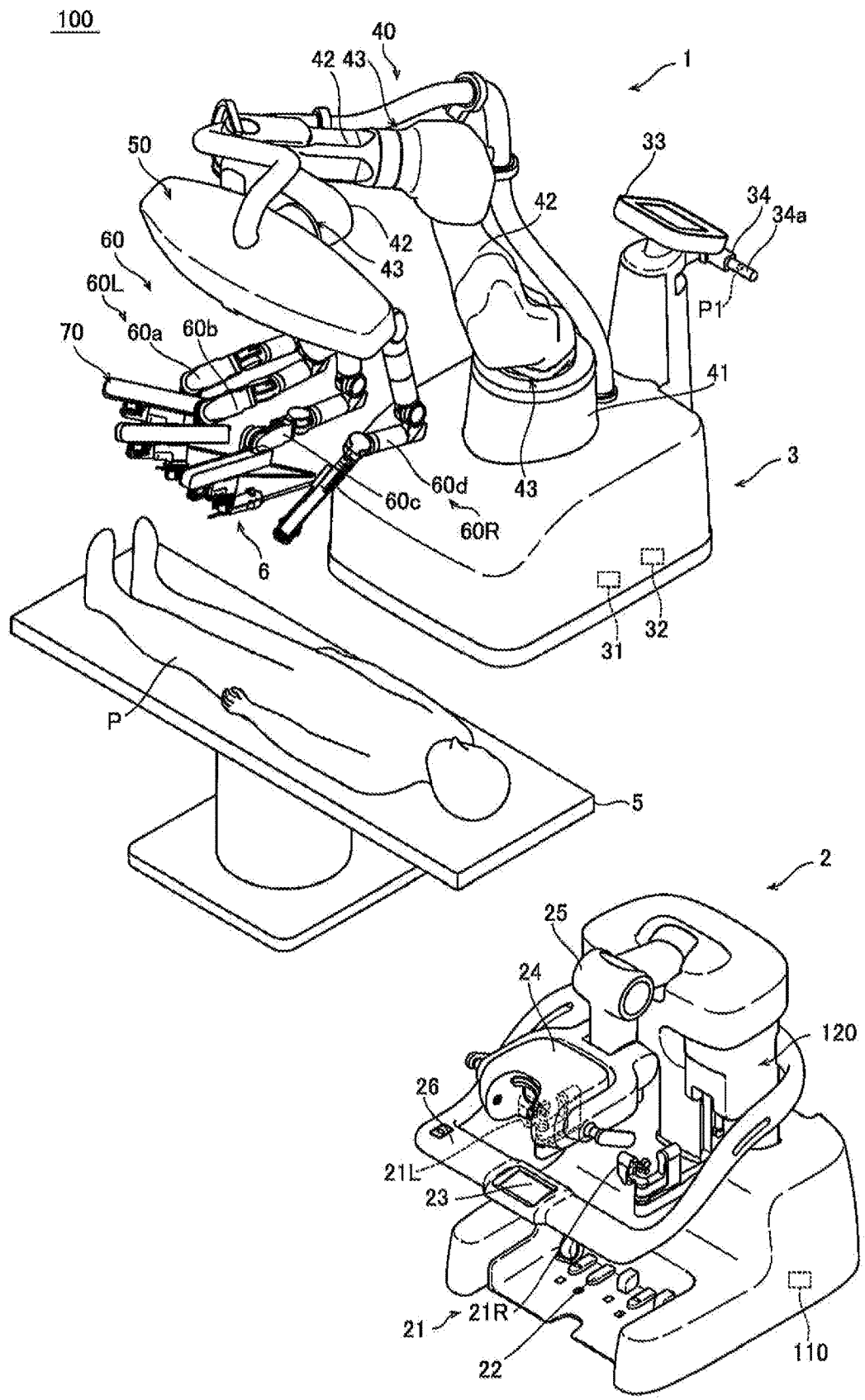
FIG. 1 is a diagram illustrating a view of a configuration of a surgical system according to a first embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

First Embodiment

With reference to FIGS. 1 to 17, a configuration of a surgical system 100 according to a first embodiment is described below. The surgical system 100 includes a medical manipulator 1 serving as a patient-side apparatus and a remote control apparatus 2 serving as an operator-side apparatus to operate the medical manipulator 1. The medical manipulator 1 is provided with a medical trolley 3 and is thus configured to be movable. The remote control apparatus 2 is provided at a location away from the medical manipulator 1. The medical manipulator 1 is configured to be remotely operated by the remote control apparatus 2. An operator or a surgeon inputs to the remote control apparatus 2 an instruction that causes the medical manipulator 1 to perform a desired operation. The remote control apparatus 2 transmits the input instruction to the medical manipulator 1. The medical manipulator 1 operates in response to the received instruction. The medical manipulator 1 is disposed in a surgery room, as a sterile field, which is sterilized. Note that the medical manipulator 1 and the remote control apparatus 2 are examples of a patient-side apparatus and a remote control apparatus, respectively.

The remote control apparatus 2 is disposed inside the surgery room or outside the surgery room, for example. The remote control apparatus 2 includes manipulator arms 21, operation pedals 22, a touch panel 23, a monitor 24, a support arm 25, and a support bar 26. The manipulator arms 21 constitute operation handles for the operator to input the instruction. Specifically, each of the manipulator arms 21 receive an amount of movement input by the operator O to operate a corresponding one of surgical instruments 4. The monitor 24 is a display (a display device) of a scope type configured to display an image captured by an endoscope 6. The support arm 25 supports the monitor 24 in such a manner that the height of the monitor 24 is adjusted to the height of the face of the operator. The touch panel 23 is disposed on the support bar 26. When a sensor(s) provided in the vicinity of the monitor 24 detects the head of the operator, the medical manipulator 1 can be operated by the remote control apparatus 2. The operator operates the manipulator arms 21 and the operation pedals 22, while viewing the surgical site displayed on the monitor 24. With this, the instruction is input to the remote control apparatus 2. The instruction that is input to the remote control apparatus 2 is transmitted to the medical manipulator 1. The manipulator arms 21 includes a manipulator arm 21R for the right hand of the operator and a manipulator arm 21L for the left hand of the operator. Note that the manipulator arm 21 is an example of an operation part (a manipulation part, or a manipulator).

Figure 3:
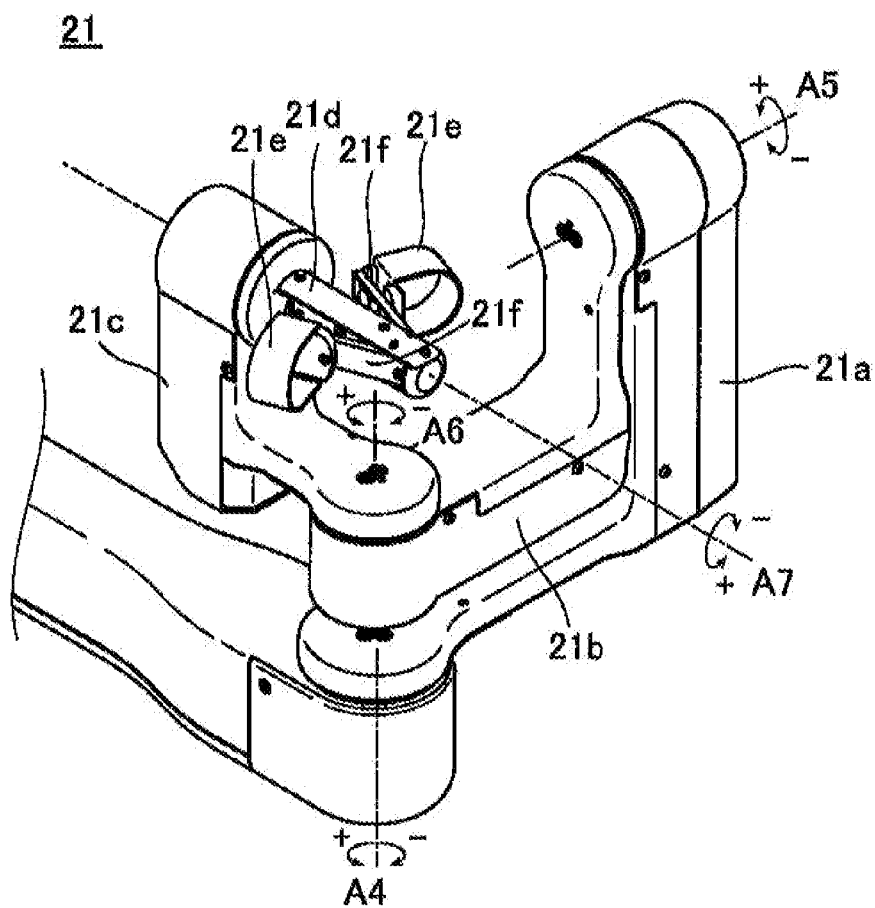
FIG. 3 is a diagram illustrating a view of a configuration of a manipulator arm of a remote control apparatus according to a first embodiment.

As illustrated in FIG. 3, each of the manipulator arms 21 includes a link portion 21a, a link portion 21b, a link portion 21c, and a link portion 21d that is to be operated by the operator such as a doctor or the like. The link portion 21a is rotatable about an axis (joint) A4. The link portion 21b is rotatable about an axis (joint) A5 with respect to the link portion 21a. The link portion 21c is rotatable about an axis (joint) A6 with respect to the link portion 21b. The link portion 21d is rotatable about an axis (joint) A7 with respect to the link portion 21c. The manipulator arm 21 is provided with a pair of grip members 21f at the link portion 21d, and each of the grip members 21f is provided with a cylindrical finger insertion portion 21e. The operator inserts fingers into the pair of finger insertion portions 21e to operate the manipulator arm 21. A proximal end of each of the pair of grip members 21f is rotatably connected to the link portion 21d. By increasing or decreasing the angle between the pair of grip members 21f, the opening angle between a first jaw member 430a and a second jaw member 430b, which will be described later, is changed.

Figure 2:
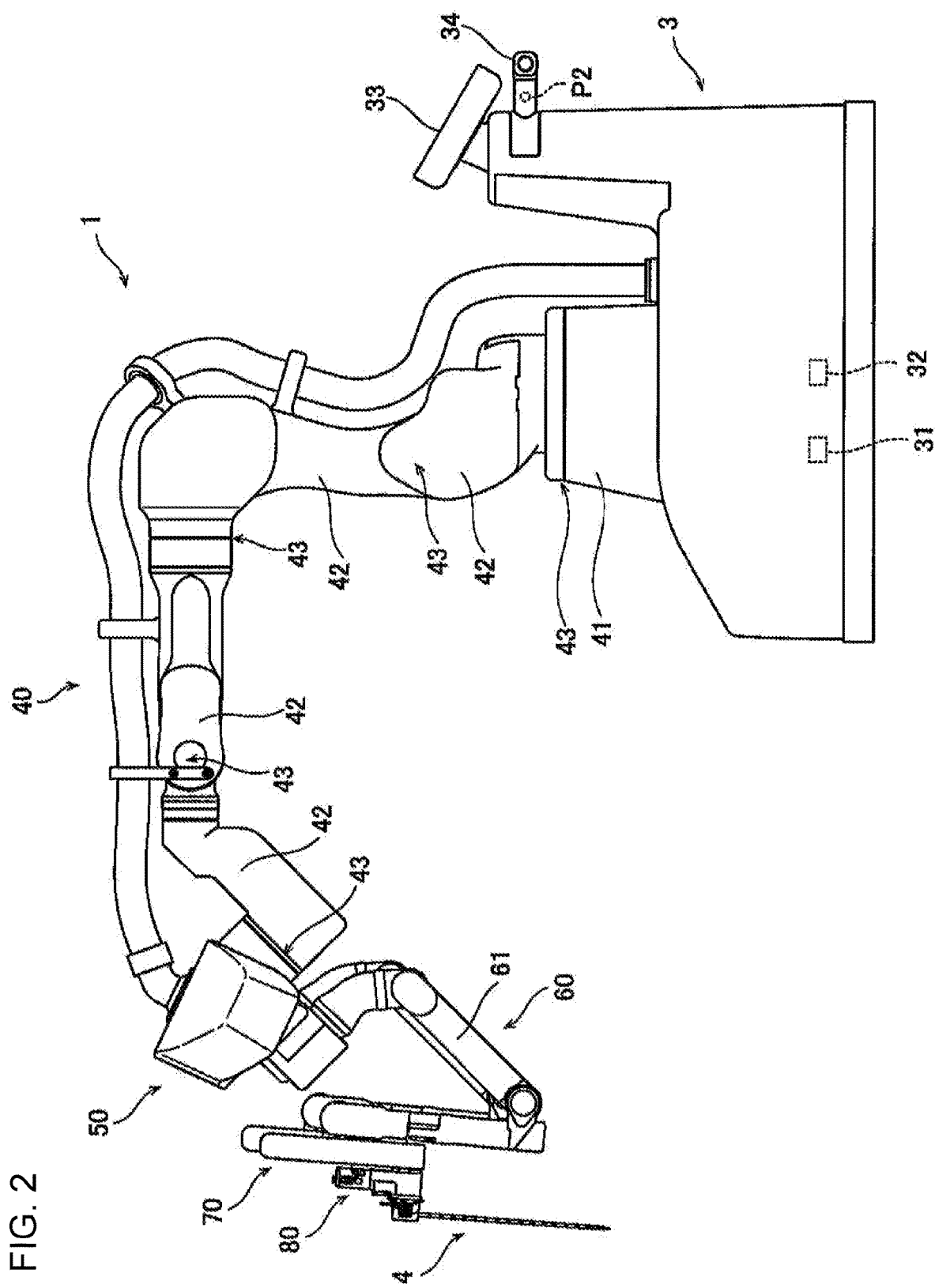
FIG. 2 is a diagram illustrating a view of a configuration of a patient-side apparatus according to a first embodiment.

As illustrated in FIGS. 1 and 2, the medical trolley 3 is provided with a control unit 31 that controls the operation of the medical manipulator 1 and a storage 32 (or a memory) that stores therein programs for controlling the operation of the medical manipulator 1. Based on the instruction inputted to the remote control apparatus 2, the control unit 31 of the medical trolley 3 controls the operation of the medical manipulator 1. Note that the control unit 31 is an example of a control device or a controller.

Further, the medical trolley 3 is provided with an input device 33. The input device 33 is configured to accept operations to move or change posture of a positioner 40, an arm base 50, and arms 60, mainly to prepare for surgery before the surgery.

As illustrated in FIGS. 1 and 2, the medical manipulator 1 is disposed in the surgery room. The medical manipulator 1 includes the medical trolley 3, the positioner 40, the arm base 50, and the arms 60. The arm base 50 is attached to a distal end of the positioner 40. The arm base 50 is a relatively long rod shape (elongate shape). Base portions (proximal end portions) of the arms 60 are attached to the arm base 50. Each of the arms 60 is configured such that the arm 60 is able to take a folded posture (storage posture). The arm base 50 and the arms 60 are used with being covered with a sterile drape.

The positioner 40 is configured as a 7-axis articulated robot. The positioner 40 is disposed on the medical trolley 3. The positioner 40 is configured to move the arm base 50. Specifically, the positioner 40 is configured to move the position of the arm base 50 three-dimensionally.

The positioner 40 includes a base portion 41 and link portions 42 connected to the base portion 41. The link portions 42 are connected to each other via joints 43

As illustrated in FIG. 1, to the distal end of each of the arms 60, the surgical instrument 4 is attached. The surgical instruments 4 include, for example, an instrument, an endoscope 6, and the like that are replaceable.

Figure 4:
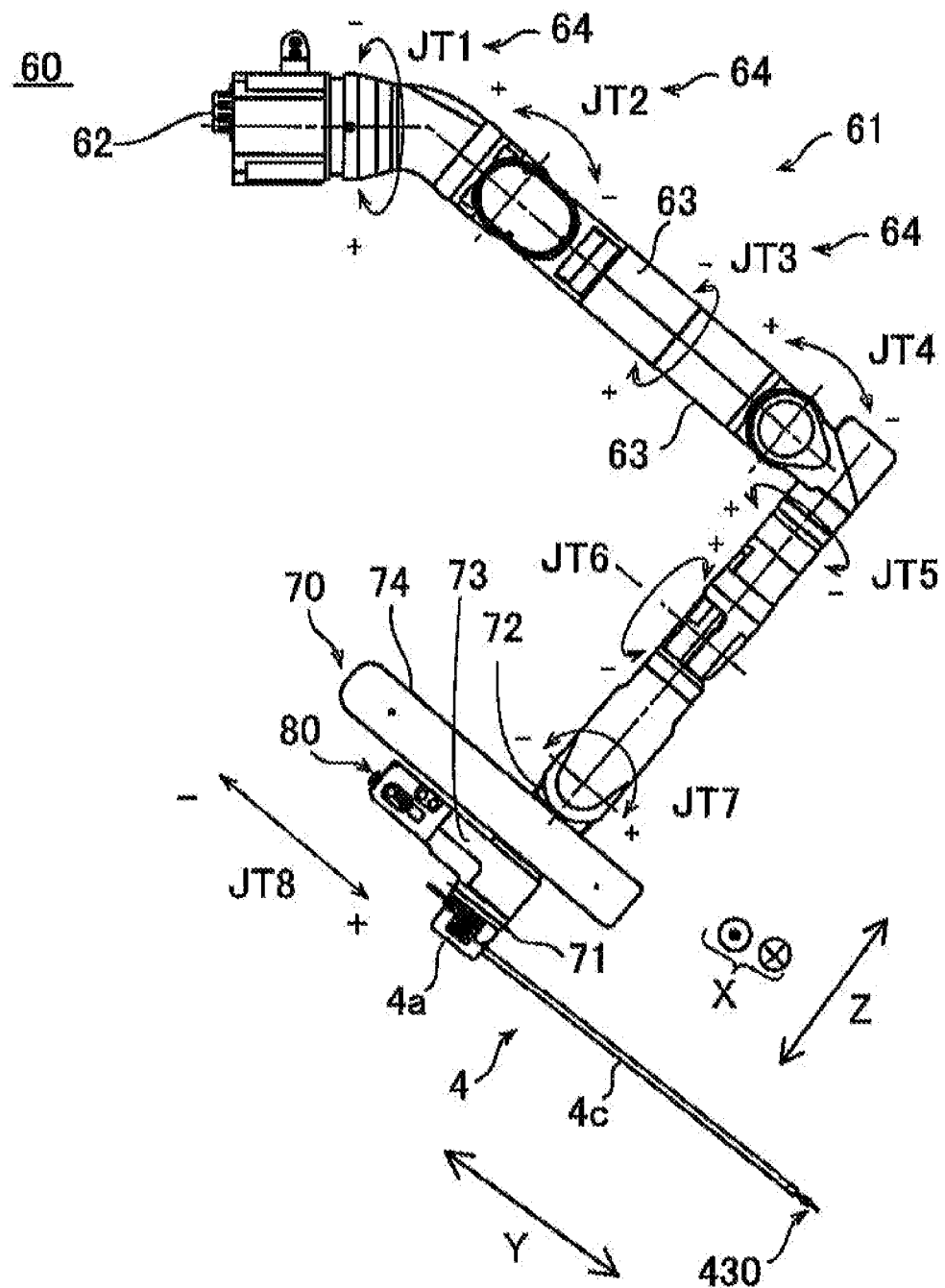
FIG. 4 is a diagram illustrating a view of a configuration of a robot arm of the patient-side apparatus according to a first embodiment.

As illustrated in FIG. 4, an end effector 430 is provided at the distal end of the instrument. Note that the end effector 430 includes two end effector members (a first jaw member 430a and a second jaw member 430b).

Next, the configuration of the arm 60 is described in detail.

As illustrated in FIG. 4, the arm 60 includes an arm section 61 and a translation movement mechanism 70 provided at the distal end portion of the arm section 61. The arm 60 is configured such that the distal end portion thereof is three-dimensionally movable with respect to the arm base 50 provided at the proximal end portion of the arm 60. Each arm 60 has 8 degrees of freedom. Specifically, the arm 60 includes the rotational axis JT1 to JT7 and a linear motion axis JT8. The plural arms 60 have the same configuration as each other. The arm section 61 includes a base portion 62, links 63, and joints 64.

The translation movement mechanism 70 is provided at the distal end portion of the arm section 61. The surgical instrument 4 is attached to the translation movement mechanism 70. The translation movement mechanism 70 translationally moves the surgical instrument 4 in the insertion direction of the surgical instrument 4 into a patient P. The translation movement mechanism 70 is configured to translationally move the surgical instrument 4 relative to the arm section 61. Specifically, the translation movement mechanism 70 is provided with the holder 71 configured to hold the surgical instrument 4. The holder 71 accommodates therein the servomotors M2 illustrated in FIG. 15. The servomotors M2 are configured to rotate rotors (rotation members) provided in the driven unit 4a of the surgical instrument 4. The surgical instrument 4 is operated by rotating the rotors (the rotation members) in the driven unit 4a.

The arm section 61 is configured as a 7-axis articulated robot arm. The arm section 61 includes the base portion 62 that connects the arm section 61 to the arm base 50 and the plural links 63 connected to the base portion 62. The plural links 63 are connected to each other via the joints 64.

The translation movement mechanism 70 is configured to translationally move the holder 71 along the Y direction so as to translationally move the surgical instrument 4 attached to the holder 71 along the Y direction (the extending direction or the longitudinal direction of the shaft 420). The translation movement mechanism 70 includes a proximal side link unit 72 connected to the distal end of the arm section 61, a distal side link unit 73, and a connecting link unit 74 provided between the proximal side link unit 72 and the distal side link unit 73. The holder 71 is provided at the distal side link unit 73.

The connecting link unit 74 of the translation movement mechanism 70 functions as a double speed mechanism that makes a movement speed of the distal side link unit 73 along the Z direction with respect to the proximal side link unit 72 twice as a movement speed of the proximal side link unit 72 along the Y direction with respect to the connecting link unit 74. The translation movement mechanism 70 is configured to translationally move the surgical instrument 4 attached to the holder 71 along the Y direction by moving the distal side link unit 73 with respect to the proximal side link unit 72 along the Z direction. The distal end of the arm section 61 is configured such that the proximal side link unit 72 is connected thereto in such a manner that the proximal side link unit 72 is rotatable about a rotational axis extending in the X direction orthogonal to the Y direction.

As illustrated in FIG. 1, the endoscope 6 is attached to one of the plural arms 60 (for example, the arm 60c), and the surgical instrument 4 other than the endoscope 6 are attached to the other arms 60 (for example, the arms 60a, 60b, and 60d). In the state where the endoscope 6 is attached to the arm 60, the pivot position for the endoscope 6 is set to the arm 60 to which the endoscope 6 is attached. Further, in the state where a pivot position setting device is attached to the arm 60 to which the surgical instrument 4 other than the endoscope 6 is attached, the pivot position for the surgical instrument 4 is set to the arm 60 to which the surgical instrument 4 other than the endoscope 6 is attached. The endoscope 6 is attached to one of two arms 60b and 60c arranged in the central area among the four arms 60 arranged adjacent to each other. That is, the pivot position is individually set for each of the plurality of arms 60.

With reference to FIGS. 5 to 14, the configurations of the surgical instrument 4, an adaptor 500, and a drape 600 are described.

In this description, the direction in which the surgical instrument 4 extends (the direction of the rotational axis JT9 of the shaft 420) is referred to as a Y direction. The direction in which the surgical instrument 4 and the adaptor 500 are adjacent to each other is defined as a Z direction, the surgical instrument 4 side along the Z direction is defined as a Z1 direction, and the opposite side of the Z1 direction is defined as a Z2 direction. Note that the rotational axis JT9 is a rotation center axis of the shaft 420. Further, the direction orthogonal to the Y direction and the Z direction is referred to as an X direction, one side along the X direction is referred as an X1 direction, and the other side along the X direction is referred to as an X2 direction.

Figure 5:
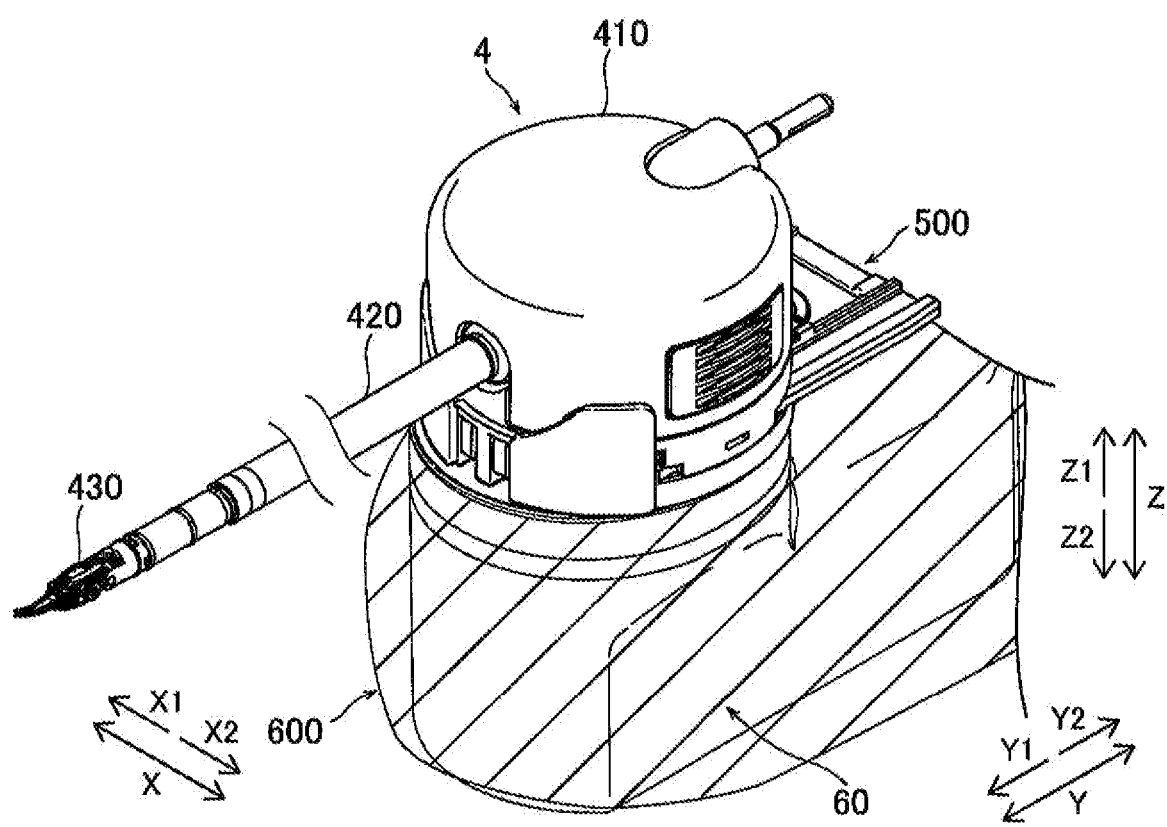
FIG. 5 is a diagram illustrating a perspective view of a state where a surgical instrument is attached to the robot arm via an adaptor according to a first embodiment.
Figure 6:
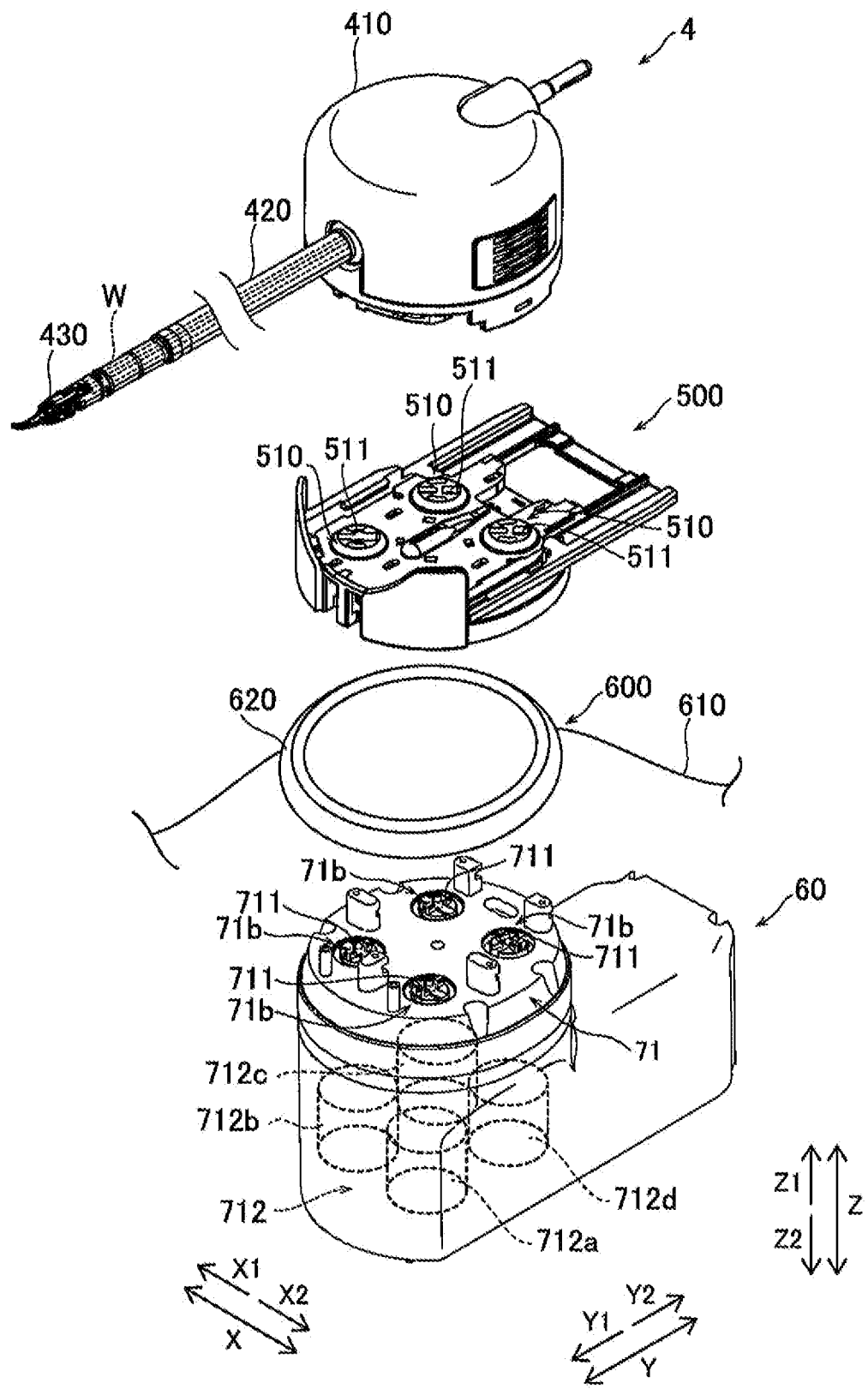
FIG. 6 is a diagram illustrating an exploded perspective view of a state where the surgical instrument is to be attached to the robot arm via the adaptor according to a first embodiment.
Figure 7:
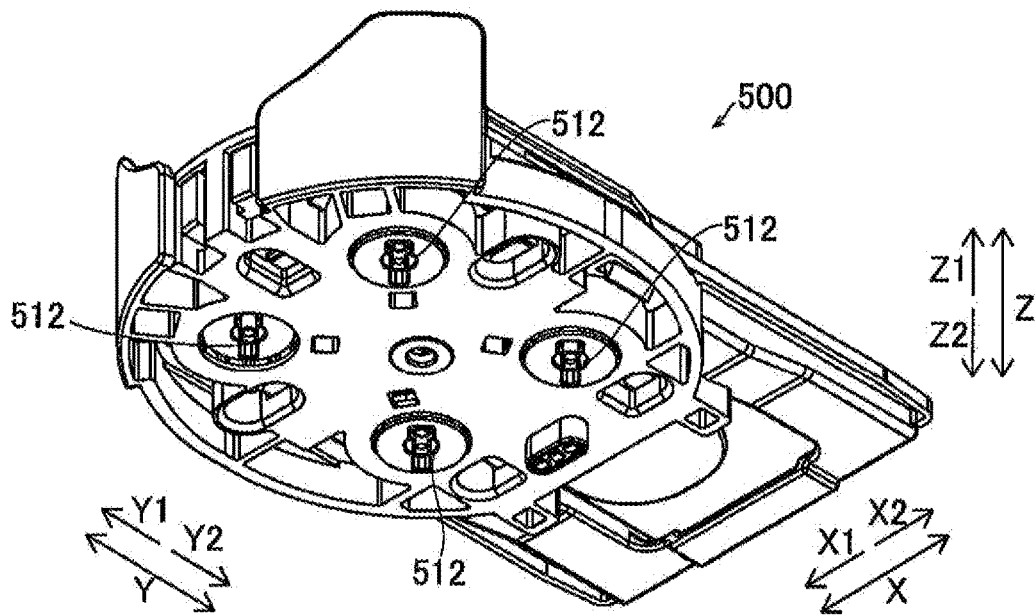
FIG. 7 is a diagram illustrating a perspective view of the adaptor according to a first embodiment as seen from below.

As illustrated in FIGS. 5 and 6, the surgical instrument 4 is detachably connected to a holder 71 of the arm 60 of the surgical system 100. Specifically, the surgical instrument 4 is detachably connected to the arm 60 through the adaptor 500. The adaptor 500 is a drape adaptor configured to sandwich a sterile drape 600 to cover the arm 60, between the adaptor 500 and the holder 71 of the arm 60.

The surgical instrument 4 is attached to the Z1 side of the adaptor 500. The adaptor 500 is attached to the Z1 side of the arm 60.

As illustrated in FIG. 6, the drape 600 includes a body section 610 that covers the arm 60 and an attachment section 620 sandwiched between the arm 60 and the adaptor 500. The body section 610 is made of a flexible film member. The flexible film member is made of a resin material, such as thermoplastic polyurethane and polyethylene. The body section 610 includes an opening so that the holder 71 of the arm 60 is engageable with the adaptor 500. To the opening of the body section 610, the attachment section 620 is provided. The attachment section 620 is made of a resin mold member. The resin mold member is made of a resin member such as polyethylene terephthalate. The attachment section 620 is harder (less flexible) than the body section 610. The attachment section 620 includes an opening so that the holder 71 is engageable with the adaptor 500.

Figure 9:
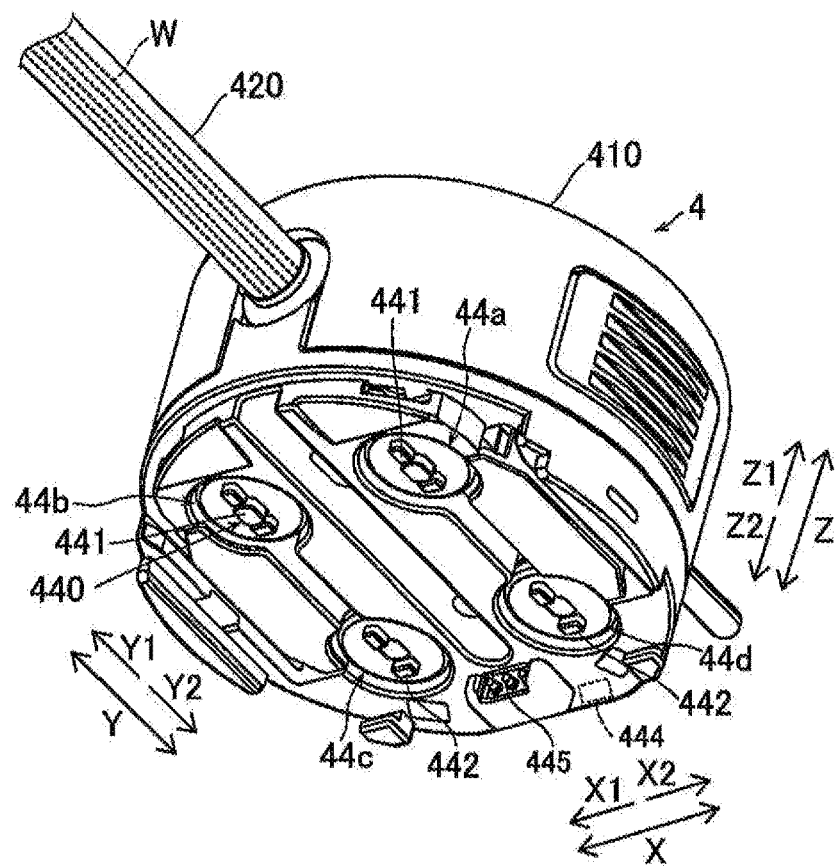
FIG. 9 is a diagram illustrating a perspective view of the surgical instrument according to a first embodiment as seen from below.
Figure 10:
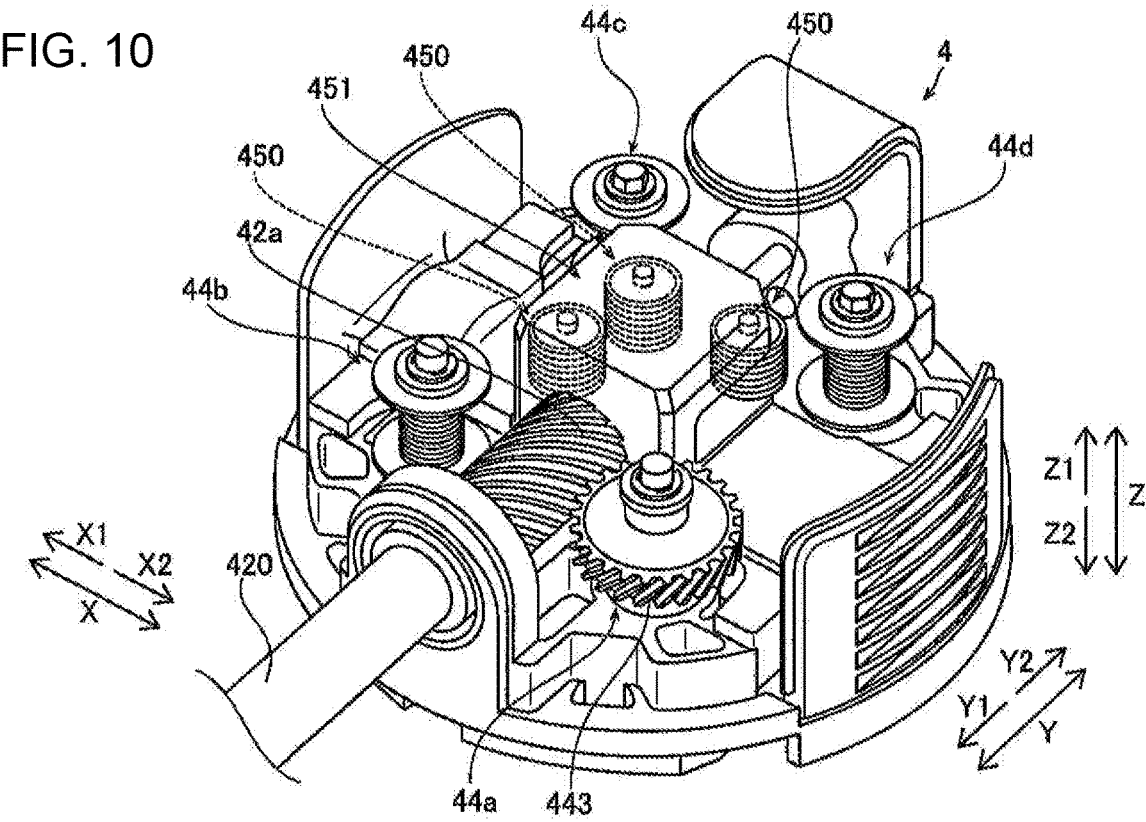
FIG. 10 is a diagram illustrating a perspective view of a state where a cover part is detached from a base body of the surgical instrument according to an embodiment.

As illustrated in FIGS. 9 and 10, the surgical instrument 4 includes plural rotation members 44a, 44b, 44c, and 44d. The rotation members 44a, 44b, 44c, and 44d are provided within the housing 410 and are rotatable about the respective rotation axes extending along the Z axis. The plural rotation members 44a, 44b, 44c, and 44d are provided to operate the end effector 430. The rotation members 44a, 44b, 44c, and 44d are connected to the end effector 430 via elongate elements W (such as wires or cables) passing through the shaft 420. With this, rotations of the rotation members 44a, 44b, 44c, and 44d drive the elongate element W, which operate the end effector 430. In addition, the rotation member 44a is connected to the shaft 420 through gears 42a. With this, the shaft 420 is rotated by the rotation of the rotation member 44a. Note that the rotation member 44c and 44d are examples of a first rotation member and a second rotation member, respectively.

To transmit driving forces from the holder 71 of the arm 60 to the end effector 430, the rotation members 44a, 44b, 44c, and 44d respectively include engagement portions 440 including projections 441 and 442, which are respectively engaged with corresponding transmission members 510 of the adaptor 500. The projection 441 or 442 is projected from the Z2 side surface of the rotation members 44a, 44b, 44c, and 44d toward the side of the adaptor 500 (the Z2 side). The projections 441 and 442 are arranged in a straight line. The projections 441 provided to the rotation members 44a and 44b have different shapes from that of the projections 442 provided to the rotation members 44c and 44d.

As illustrated in FIG. 6, the adaptor 500 includes a plurality of the drive transmission members 510. The drive transmission members 510 are configured to transmit driving forces from the arm 60 to the rotation members 44a, 44b, 44c, and 44d of the surgical instrument 4. That is, the drive transmission members 510 are provided four so as to correspond to the rotation members 44a, 44b, 44c, and 44d of the surgical instrument 4. The drive transmission members 510 are rotatable about the respective rotation axes, which extend along the Z direction.

Each of the drive transmission members 510 includes an engagement portion 511 including an engagement recess which is engaged with the projection 441 or 442 of the corresponding rotation members 44a, 44b, 44c, and 44d of the surgical instrument 4. The engagement recess provided to the engagement portion 511 is located at the surgical instrument 4 side (the Z1 side) of the drive transmission member 510 and is recessed from the Z1 side surface of the drive transmission member 510, toward the Z2 side, opposite to the surgical instrument 4. Each of the drive transmission members 510 is provided at the Z2 side surface thereof with the engagement portion 512 illustrated in FIG. 7 including the engagement recess, which is respectively engaged with a projection provided to the engagement portion 711 of the corresponding drive part 71b of the holder 71.

Figure 8:
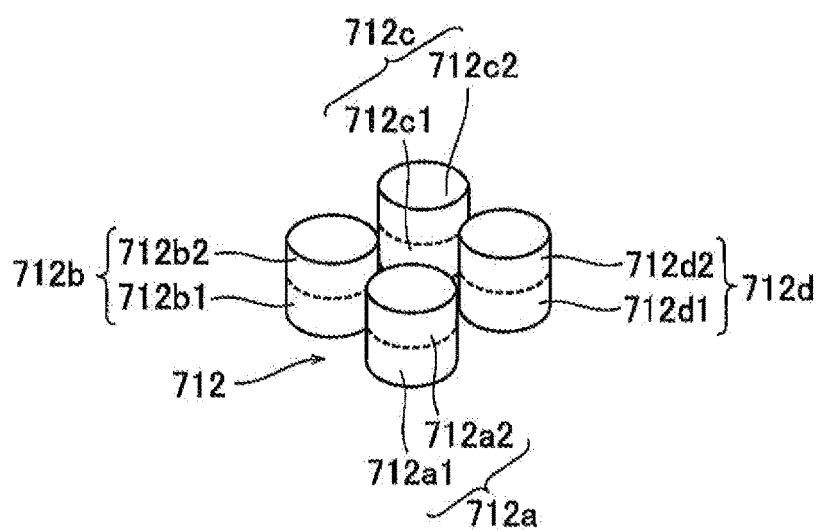
FIG. 8 is a diagram illustrating a view of actuators according to a first embodiment.

The holder 71 of the arm 60 includes plural drive parts 71b. The plural drive parts 71b are provided corresponding to the plural drive transmission members 510 of the adaptor 500. Each of the drive parts 71b includes the engagement portion 711 and an actuator 712. Note that the drive parts 71b and the drive transmission members 510 are provided four respectively. The actuators 712 include four actuators 712a, 712b, 712c, and 712d. As illustrated in FIG. 8, the actuator 712a includes a servomotor 712a1 and a speed reducer 712a2, the actuator 712b includes a servomotor 712b1 and a speed reducer 712b2, the actuator 712c includes a servomotor 712c1 and a speed reducer 712c2, and the 712d includes a servomotor 712d1 and a speed reducer 712d2. Reduction ratios of the speed reducers 712a2 to 712d2 (reduction gears) are 10 to 150. The speed reducers 712a2 to 712d2 converts the amount of rotation (rotation angle) of the servomotors 712a1 to 712d1 to 1/10 to 1/150 times and outputs the reduced rotation amount (the reduced rotation angle) so as to rotate the engaging portions 711, the drive transmission members 510 engaged with the engagement portions 711, the engagement portions 440 engaged with the drive transmission members 510, and the rotation members 44a to 44d connected to the engagement portions 440. It may be preferable that the reduction ratio of the speed reducers 712a2 to 712d2 is 30 to 120, the reduction ratio of the speed reducers 712a2 is 100, and the reduction ratio of the speed reducers 712b2 to 712d2 is 50. Note that the servomotors 712c1 and 712d1 are examples of a first drive part and a second drive part, respectively.

The engagement projection provided to the engagement portion 711 is engaged with the engagement recess provided to the engagement portion 512 of the corresponding drive transmission member 510. The engagement projection of the engagement portion 711 is projected from the Z1 side surface of the drive part 71b toward the Z1 side (the adaptor 500 side).

The actuators 712 include the servomotors 712a1 to 712d1 (corresponding to M2 illustrated in FIG. 15), the speed reducers 712a2 to 712d2 (not illustrated in FIG. 15), and encoders (corresponding to E2 in FIG. 15) that detect the rotation angles of the servomotors 712a1 to 712d1. The servomotors 712a1 to 712d1 (corresponding to M2 in FIG. 15) and the speed reducers 712a2 to 712d2 (not illustrated in FIG. 15) of the actuator 712 are configured to drive the engagement portions 711 to rotate about the rotational axes thereof extending in the Z direction. Thereby, the drive transmission members 510 of the adaptor 500 engaged with the engagement portions 711 can be rotated about the rotational axes thereof extending in the Z direction, and the rotation members 44a, 44b, 44c, and 44d of the surgical instrument 4 engaged with the drive transmission members 510 can be rotated about the rotational axes thereof.

Figure 11:
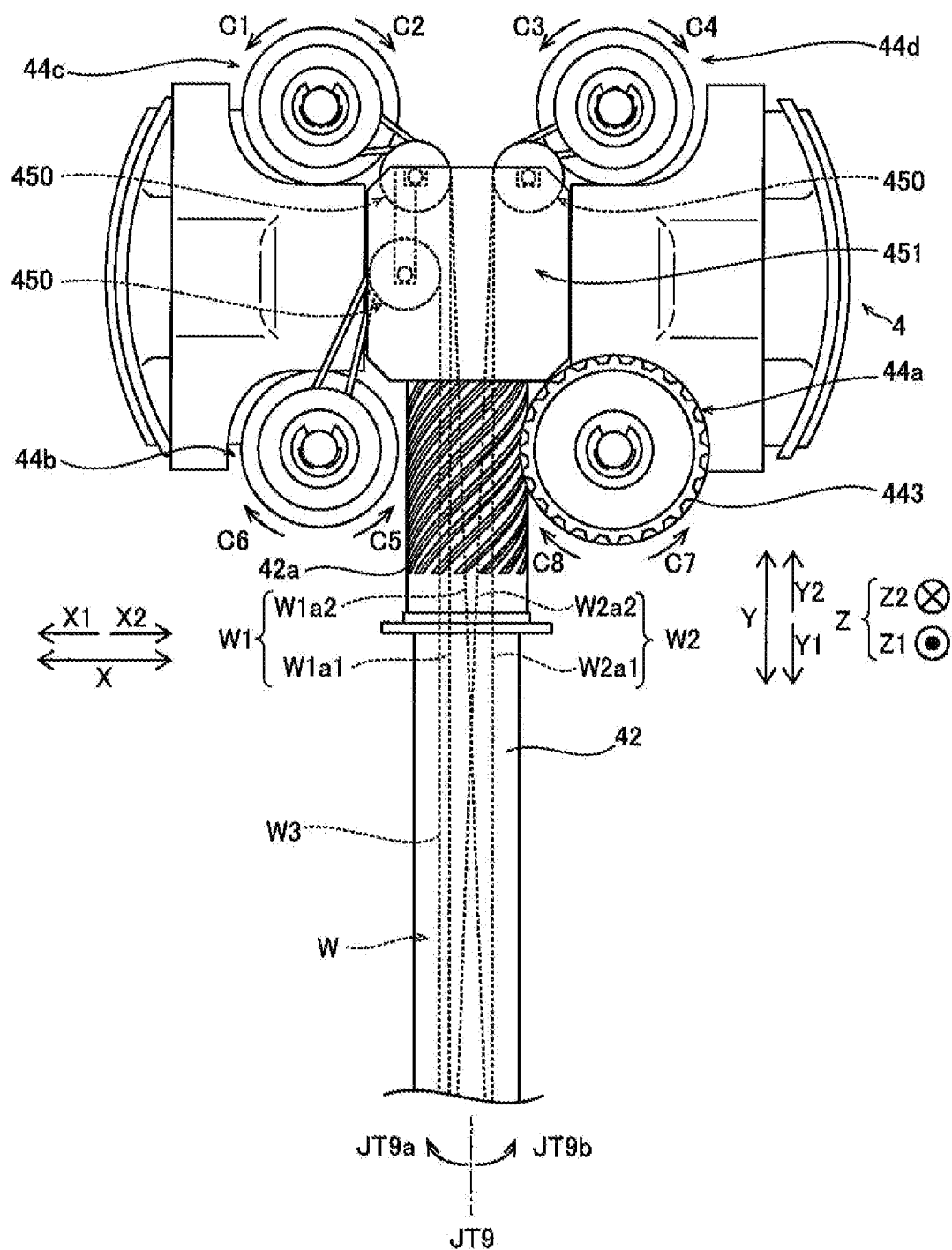
FIG. 11 is a diagram illustrating a plan view of a state where the cover part is detached from the base body of the surgical instrument according to a first embodiment.

As illustrated in FIGS. 10 and 11, the elongate elements W are wound around the rotation members 44b to 44d of the surgical instrument 4. Specifically, a first portion W3a1 of the third elongate element W3 is wound clockwise around an upper portion of the rotation member 44b, and a second portion W3a2 of the third elongate element W3 is wound counterclockwise around a lower portion of the rotation member 44b.

The first elongate element W1 includes a first portion W1a1, a second portion W1a2, and a stopper or an attachment W1b such as a bead or the like provided between the first portion W1a1 and the second portion W1a2. The attachment W1b is fixed to the first jaw member 430a. The end portion of the first portion W1a1 of the first elongate element W1 is wound counterclockwise around the upper portion of the rotation member 44c. The end portion of the second portion W1a2 of the first elongate element W1 is wound clockwise around the lower portion of the rotation member 44b. Note that the attachment W1b is an example of a first fixation portion (or a first attachment).

The second elongate element W2 includes a first portion W2a1, a second portion W2a2, and a stopper or an attachment W2b provided between the first portion W2a1 and the second portion W2a2. The attachment W2b is fixed to the second jaw member 430b. Further, the end portion of the first portion W2a1 of the second elongate element W2 is wound counterclockwise around the upper portion of the rotation member 44d. The end portion of the second portion W2a2 of the second elongate element W2 is wound clockwise around the lower part of the rotation member 44d. Note that the first portion W2a1, the second portion W2a2, and the attachment W2b are examples of a third portion, a fourth portion, and a second fixation portion (a second attachment), respectively.

The elongate elements W extend from the rotation members 44b to 44d through the shaft 420 to the end effector 430, are wound around the end effector 430, return to the rotation members 44b to 44d through the shaft 420. Further, the elongate elements W are wound around built-in pulleys 450 in the housing 410, respectively. The built-in pulleys 450 are retained by a pulley retainer 451.

Figure 12:
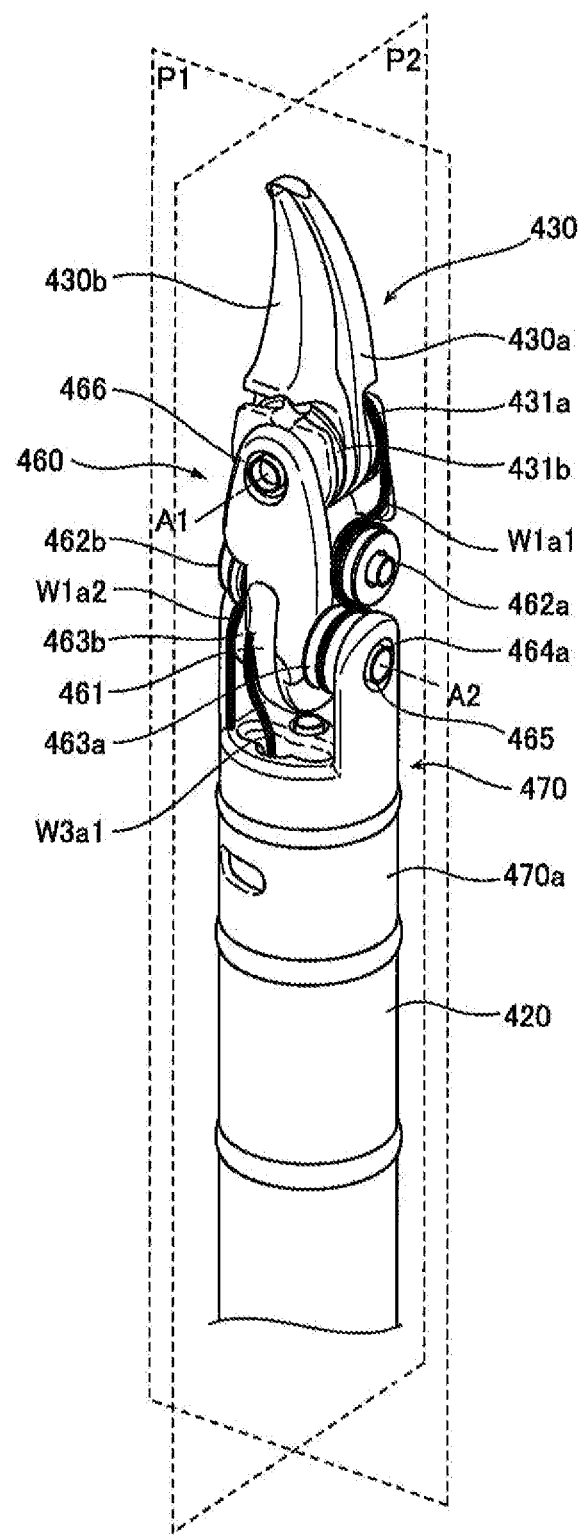
FIG. 12 is a diagram illustrating a perspective view of the end effector of the surgical instrument according to a first embodiment.

As illustrated in FIGS. 11 and 12, the rotation member 44x is rotated about the rotation axis thereof to operate (drive) the first jaw member 430a. Specifically, the rotation member 44c is rotated by the servomotor 712c1 to drive the first elongate element W1. The first elongate element W1 extends through the inside of the shaft 420 and connects the first jaw member 430*a* and the rotation member 44*c*. When the rotation member 44*c* is rotated in the C1 direction illustrated in FIG. 11 to draw the first portion W1*a*1 of the first elongate element W1, the first jaw member 430*a* is driven to move in the C1*a* direction illustrated in FIG. 13 (the direction to open the first jaw member 430*a*). When the rotation member 44*c* is rotated in the C2 direction illustrated in FIG. 11, opposite to the C1 direction, to draw the second portion W2*a*1 of the first elongate element W1, the first jaw member 430*a* is driven to move in the C2*a* direction illustrated in FIG. 13 (the direction to close the first jaw member 430*a*). Note that in FIG. 12, the second elongate element W2 is omitted.

The rotation member 44*d* is rotated about the rotation axis thereof to operate (drive) the second jaw member 430*b*. Specifically, the rotation member 44*d* is rotated by the servomotor 712*d*1 to drive the second elongate element W2. The second elongate element W2 extends through the inside of the shaft 420 and connects the second jaw member 430*b* and the rotation member 44*d*. When the rotation member 44*d* is rotated in the C3 direction illustrated in FIG. 11 to draw the first portion W2*a*1 of the second elongate element W2, the second jaw member 430*b* is driven to move in the C3*a* direction illustrated in FIG. 13 (the direction to open the second jaw member 430*b*). When the rotation member 44*d* is rotated in the C4 direction illustrated in FIG. 11, opposite to the C3 direction, to draw the second portion W2*a*2 of the second elongate element W2, the second jaw member 430*b* is driven to move in the C4*a* direction illustrated in FIG. 13 (the direction to close the second jaw member 430*b*).

By being rotated about the rotation axis thereof, the rotation member 44*b* operates a distal clevis 460, which is a wrist portion of the end effector 430. Specifically, the rotation member 44*b* is rotated to drive the third elongate element W3. When the rotation member 44*b* is rotates in the C5 direction (illustrated in FIG. 11), to draw the first portion W3*a*1 of the third elongate element W3, the distal clevis 460 is driven to move in the C5*a* (illustrated in FIG. 13). When the rotation member 44*b* is rotated in the C6 direction (illustrated in FIG. 11), which is opposite to the C5 direction, the distal clevis 460 is driven to move in the C6*a* direction (illustrated in FIG. 13), which is opposite to the C5*a* direction.

When the rotation member 44*a* is rotated about the rotation axis thereof with the gear portion 443 of the rotation member 44*a* being engaged with a gear portion 42*a* connected to the proximal end of the shaft 420, the shaft 420 is rotationally driven to rotate the end effector 430. Specifically, when the rotation member 44*a* is rotated in the C7 direction illustrated in FIG. 11, the shaft 420 is driven to rotate in a first direction and thus the end effector 430 is driven to rotate in the first direction. To the contrary, when the rotation member 44*a* is rotated in the C8 direction illustrated in FIG. 11, the shaft 420 is driven to rotate in a second direction opposite to the first direction and thus the end effector 430 is driven to rotate in the second direction. The shaft 420 is driven to rotate by the rotation of the actuator 712*a*.

In other words, in a first embodiment, as illustrated in FIG. 11, the rotation member 44*c* is arranged on the proximal end side of the shaft 420, and is rotated by the rotation of the actuator 712*c* to drive the first elongate element W1. The rotation member 44*d* is arranged on the proximal end side of the shaft 420, and is rotated by the rotation of the actuator 712*d* to drive the second elongate element W2. The first jaw member 430*a* and the second jaw member 430*b* are arranged at the distal end of the shaft 420 via the distal clevis 460.

In the state where the rotation angle of the shaft 420 is zero, the second portion W1*a*2 of the first elongate element W1 that drives the first jaw member 430*a* and the second portion W2*a*2 of the second elongate element W2 that drives the second jaw member 430*b* are arranged so as to intersect each other in the shaft 420. Note that the first portion W1*a*1 of the first elongate element W1 that drives the first jaw member 430*a* and the first portion W2*a*1 of the second elongate element W2 that drives the second jaw member 430*b* are arranged parallel to each other along the rotation axis JT9 of the shaft 420.

In FIG. 12, the first portion W1*a*1 of the first elongate element W1 is guided by inner pulleys, which are pulleys that are provided on the side closer to the second plane P2 in a group of first pulleys 462*a* and a group of second pulleys 463*a*, and is guided to the rotation member 44*c* along the rotation axis JT9 of the shaft 420. To the contrary, in FIG. 14, the second portion W1*a*2 of the first elongate element W1 is guided by outer pulleys, which are pulleys that are provided on the side farther from the second plane P2 in a group of first pulleys 462*b* and a group of second pulleys 463*b*, and is guided to the rotation member 44*c* across the rotation axis JT9 of the shaft 420. Therefore, as illustrated in FIG. 11, the first portion W1*a*1 of the first elongate element W1 is arranged substantially parallel to the rotation axis JT9 of the shaft 420, and the second portion W1*a*2 of the first elongate element W1 is arranged so as to intersect the rotation axis JT9. For the same reason as for the first elongate element W1, the first portion W2*a*1 of the second elongate element W2 is arranged substantially parallel to the rotation axis JT9, and the second portion W2*a*2 of the second elongate element W2 is arranged so as to intersect the rotation axis JT9.

Further, in a first embodiment, the first elongate element W1 and the second elongate element W2 are twisted 180 degrees, from the state illustrated in FIG. 11, with respect to the rotation axis JT9 of the shaft 420 between the first jaw member 430*a* and the second jaw member 430*b* in the shaft 420. Specifically, in a state where the distal clevis 460 to which the first jaw member 430*a* and the second jaw member 430*b* are attached is rotated 180 degrees around the rotation axis JT9 of the shaft 420 after the attachment W1*b* of the first elongate element W1 and the attachment W2*b* of the second elongate element W2 are attached to the first jaw member 430*a* and the second jaw member 430*b*, the end portion of the first portion W1*a*1 and the end portion of the second portion W1*a*2 of the first elongate element W1 are wound around the rotation member 44*c*, and the end portion of the first portion W2*a*1 and the end portion of the second portion W2*a*2 of the second elongate element W2 are wound around the rotation member 44*d*.

Figure 13:
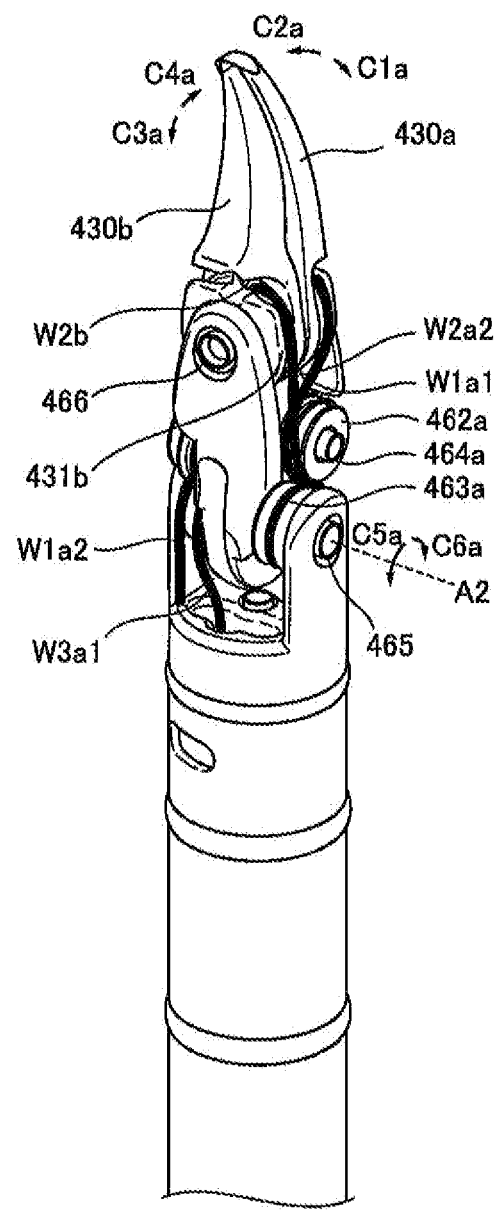
FIG. 13 is a diagram illustrating a perspective view of the end effector of the surgical instrument according to a first embodiment.
Figure 14:
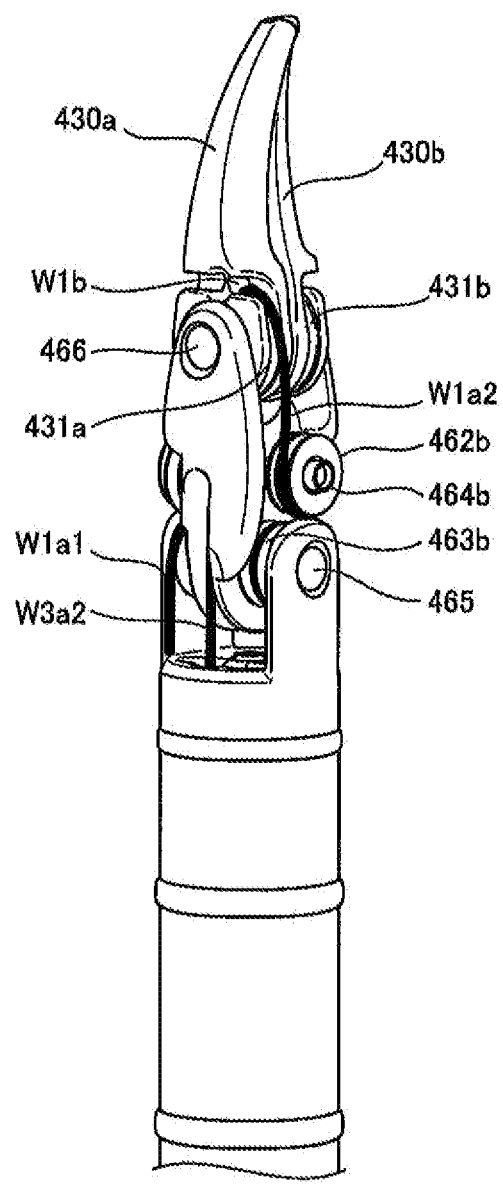
FIG. 14 is a diagram illustrating a perspective view of the end effector of the surgical instrument according to a first embodiment.

As illustrated in FIGS. 12 to 14, the surgical instrument 4 is, for example, an electrosurgical instrument such as a monopolar curved scissors. The surgical instrument 4 includes a conductive end effector 430, a conductive distal clevis 460 that rotatably supports the end effector 430 about a first axis A1, and a conductive proximal clevis 470 that rotatably supports the distal clevis 460 about a second axis A2. The surgical instrument 4 includes the shaft 420 having a cylindrical shape and connected to the proximal clevis 470.

As illustrated in FIG. 12, the end effector 430 includes two end effector members, which are the first and second jaw members 430*a* and 430*b*. Each of the first and second jaw members 430a and 430b is, for example, made of a conductive member such as stainless steel or the like.

Specifically, the first jaw member 430a includes a pulley portion 431a and the second jaw member 430b includes a pulley portion 431b. The first jaw member 430a is configured to change the posture thereof along with the movement of the first portion W1a1 and the second portion W1a2 of the first elongate element W1 wound around the pulley portion 431a. More specifically, as illustrated in FIG. 14, the attachment W1b formed in a circular-column shape of the first elongate element W1 is engaged with the pulley portion 431a of the first jaw member 430a. As the first elongate element W1 moves, the pulley portion 431a rotates about a first axis A1, which will be described later, and thus the first jaw member 430a rotates about the first axis A1. As illustrated in FIG. 13, the second jaw member 430b includes a pulley portion 431b. The second jaw member 430b is configured to change the posture thereof along with the movement of the first portion W2a1 and the second portion W2a2 of the second elongate element W2 wound around the pulley portion 431b. Here, in a first embodiment, the end effector 430 is scissors as described above.

The distal clevis 460 includes: the pulley portion 461; the first pulley group 462a which includes two pulleys rotatable about a first shaft portion 464a; the first pulley group 462b which includes two pulleys rotatable about a first shaft portion 464b; the second pulley groups 463a and 463b, each of which includes two pulleys rotatable about a second shaft portion 465; and a third shaft portion 466. The first pulley group 462a, the second pulley group 463a, and the first shaft portion 464a are arranged on one side of the distal clevis 460 with respect to the second plane P2 illustrated in FIG. 11. The first pulley group 462b, the second pulley group 463b, and the first shaft portion 464b are arranged on the other side of the distal clevis 460 with respect to the second plane P2 illustrated in FIG. 12. Each pulley included in the first pulleys 462a and 462b has a smaller diameter than each pulley included in the second pulleys 463a and 463b.

At the distal end side (the end effector 430 side) of the distal clevis 460, a pair of shaft holes are formed. The third shaft portion 466, which rotatably supports the pulley portion 431a of the first jaw member 430a and the pulley portion 431b of the second jaw member 430b, is inserted in a pair of shaft holes. The third shaft portion 466 is a shaft member formed in a cylindrical column shape extending along the first axis A1. The third shaft portion 466 is supported by the pair of shaft holes. The first axis A1 extends along a direction substantially orthogonal to the rotation axis JT9 of the shaft 420. The first axis A1 extends in the direction substantially orthogonal to the first plane P1 and substantially parallel to the second plane P2.

The pulley portion 461 is provided on a proximal end side of the distal clevis 460 (on the shaft 420 side) and is rotatably supported about the second axis A2 by the proximal clevis 470. Specifically, the pulley portion 461 is rotatably supported by the second shaft portion 465 which is supported by the proximal clevis 470. The second axis A2 extends along the direction substantially orthogonal to the rotation axis JT9 of the shaft 420 and substantially orthogonal to a direction parallel to the first axis A1. The second axis A2 extends in the direction substantially parallel to the first plane P1 and substantially orthogonal to the second plane P2. The pulley portion 461 includes a pulley groove formed along a circumferential direction of the second axis A2. The distal clevis 460 is configured to change the posture thereof as a third elongate element W3 wound around the pulley portion 461 thereof moves. More specifically, a cylindrical column shaped attachment of the third elongate element W3 is engaged with the pulley portion 461. When the second elongate element W3 moves, the pulley portion 461 rotates about the second rotational axis A2 and thus rotates the distal clevis 460 about the second rotational axis A2. The cylindrical column shaped attachment is provided between the first portion W3a1 and the second portion W3a2 of the third elongate element W3. The third elongate element W3 is driven by the actuator 712b.

The two pulleys of the first pulley group 462a are rotatably supported by the first shaft portion 464a. Two pulleys of the second pulley group 463a are rotatably supported by the second shaft portion 465. In FIG. 12, the pulley that is provided on the side closer to the second plane P2 in the first pulley group 462a (the inner pulley of the first pulley group 462a) and the pulley that is provided on the side closer to the second plane P2 in the second pulley group 463a (the inner pulley of the second pulley group 463a) guide the first portion W1a1 of the first elongate element W1 engaged with the pulley portion 431a of the first jaw member 430a. On the other hand, in FIG. 14, the pulley that is provided on the side far from the second plane P2 in the first pulley group 462b (the outer pulley of the first pulley group 462b) and the pulley that is provided on the side far from the second plane P2 in the second pulley group 463b (the outer pulley of the second pulley group 463b) guide the second portion W1a2 of the first elongate element W1 engaged with the pulley portion 431b of the second jaw member 430b. The first pulley groups 462a and 462b are arranged between the second axis A2 and the first axis A1. The second pulleys 463a and the second pulleys 463b are arranged on the second axis A2. More specifically, the cylindrical column-shaped attachment W1b of the first elongate element W1 is engaged with the pulley portion 431a. When the first elongate element W1 moves, the pulley portion 431a rotates about the first rotational axis A1 and thus the first jaw member 430a rotates about the first rotational axis A1. As illustrated in FIG. 13, the circular-column shaped attachment W2b of the second elongate element W2 is engaged with the pulley portion 431b. As the second elongate element W2 moves, the pulley portion 431b rotates about the first axis A1 and thus the second jaw member 430b rotates about the first axis A1. The pulley that is provided on the side far from the second plane P2 in the first pulley group 462b (the outer pulley of the first pulley group 462b) and the pulley that is provided on the side farther from the second plane P2 in the second pulley group 463b (the outer pulley of the second pulley group 463b) guide the second portion W2a2 of the second elongate element W2 engaged with the pulley portion 431b of the second jaw member 430b.

The first shaft portion 464a extends along a rotation axis (a rotation center) substantially parallel to the second shaft A2, and is arranged on the same side as the pulley portion 431a with respect to the first plane P1. The first shaft portion 464b is arranged on the same side as the pulley portion 431b with respect to the first plane P1. The second shaft portion 465 is a shaft member formed in a cylindrical column shape extending along the second axis A2. The second shaft portion 465 is inserted in and supported by a pair of shaft holes of the proximal clevis 470.

Here, each of the first elongate element W1, the second elongate element W2, and the third elongate element is a wire or a cable. Each of the first elongate element W1, the second elongate elements W2, and third elongate element W3 is made of a metal such as stainless steel, tungsten, or the like. The third elongate element W3 is provided corresponding to the pulley portion 461. The first elongate element W1 and the second elongate element W2 are provided corresponding to the first jaw member 430a and the second jaw member 430b. Note that a part of each of first elongate element W1, the second elongate elements W2, and third elongate element W3 may be made of a rod or the like.

As illustrated in FIG. 12, the proximal clevis 470 includes a connection base portion 470a connected to the shaft 420.

Figure 15:
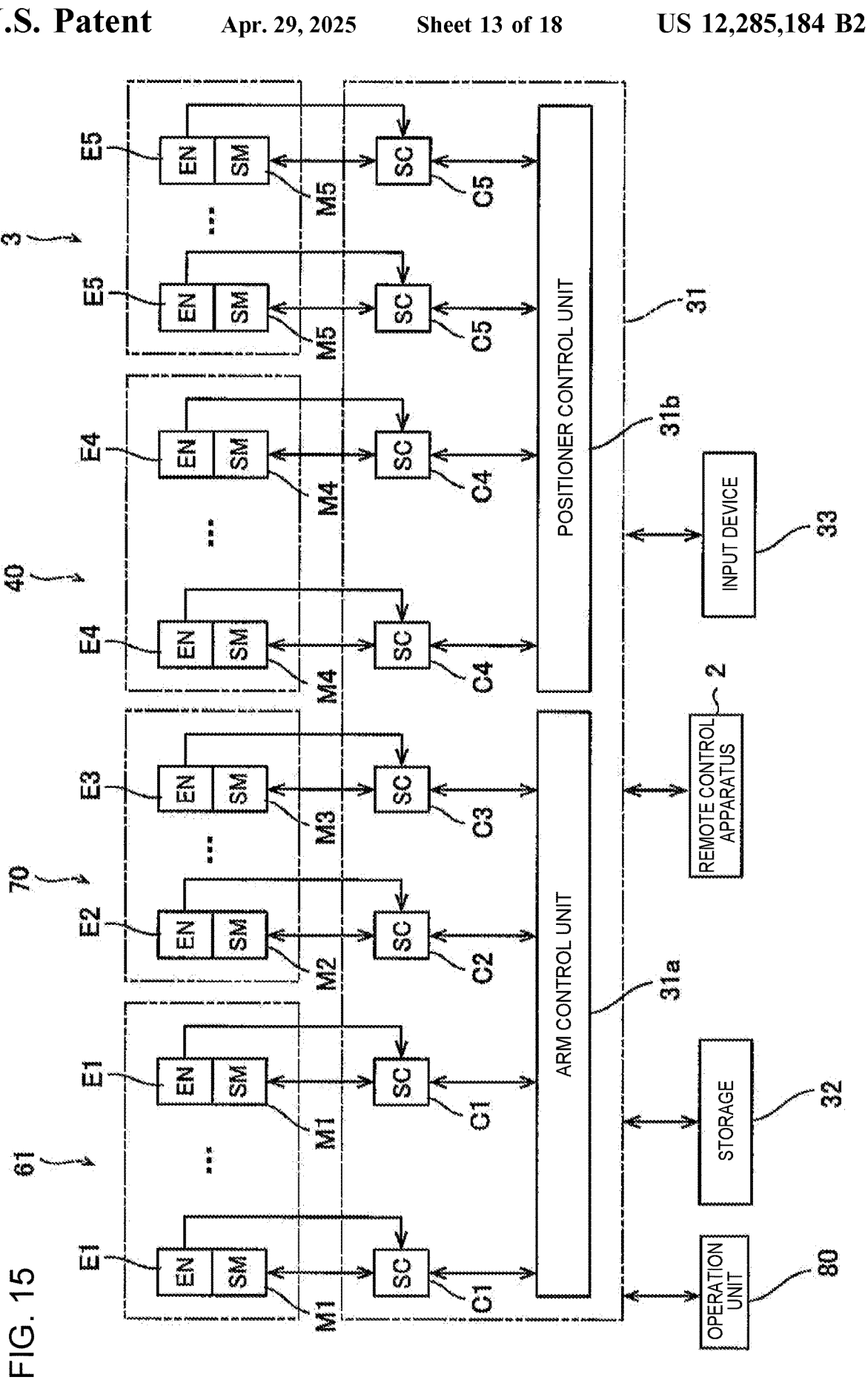
FIG. 15 is a block diagram illustrating a view of a configuration of a control unit of the surgical system according to a first embodiment.

As illustrated in FIG. 15, the arm 60 is provided with a plurality of servomotors M1, a plurality of encoders E1, and a plurality of speed reducers (not illustrated in FIG. 15), so as to correspond to the plurality of joints 64 of the arm section 61. The encoder E1 is configured to detect the rotation angle of the servomotor M1. The speed reducer is configured to reduce the rotation of the servomotor M1 to increase the torque.

As illustrated in FIG. 15, the translational movement mechanism 70 includes the servomotors M2 for rotating the rotors (rotation members) provided in the driven unit 4a of the surgical instrument 4, a servomotor M3 for translationally moving the surgical instrument 4, encoders E2 and E3, and speed reducers (not illustrated in FIG. 15). Note that the servomotors M2 illustrated in FIG. 15 correspond to the actuators 712 illustrated in FIG. 6. The encoders E2 and the encoder E3 are configured to detect the rotation angles of the servomotors M2 and the servomotor M3, respectively. The speed reducers are configured to reduce the rotations of the servomotors M2 and the servomotor M3 to increase the torque thereof.

The positioner 40 is provided with a plurality of servomotors M4, a plurality of encoders E4, and a plurality of speed reducers (not illustrated), so as to correspond to the plurality of joints 43 of the positioner 40. The encoders E4 detect the rotation angles of the servomotors M4. The speed reducers are configured to reduce the rotations of the servomotors M4 to increase the torque thereof.

The medical trolley 3 is provided with servomotors M5 that drive a plurality of front wheels (not illustrated) of the medical trolley 3 respectively, encoders E5, and speed reducers (not illustrated) The encoders E5 detect the rotation angles of the servomotors M5. The speed reducer is configured to reduce the rotation of the servomotor M5 to increase the torque.

The control unit 31 of the medical trolley 3 includes an arm control unit 31a that controls the movement of the plurality of arms 60 based on commands, and a positioner control unit 31b that controls the movement of the positioner 40 and driving of the front wheel (not illustrated) of the medical trolley 3 based on commands. A servo control unit C1 that controls the servomotors M1 for driving the arm 60 is electrically connected to the arm control unit 31a. Further, an encoder E1 that detects the rotation angle of the servomotor M1 is electrically connected to the servo control unit C1.

A servo control unit C2 that controls the servomotors M2 for driving the surgical instrument 4 is electrically connected to the arm control unit 31a. The encoders E2 that detect the rotation angles of the servomotors M2 are electrically connected to the servo control unit C2. The servo control unit C3 that controls the servomotor M3 for translationally moving by the translational movement mechanism 70 is electrically connected to the arm control unit 31a. The encoder E3 for detecting the rotation angle of the servomotor M3 is electrically connected to the servo control unit C3.

The operation command input to the remote control apparatus 2 is input to the arm control unit 31a. The arm control unit 31a generates position commands based on the operation command inputted and the rotation angles detected by the encoders E1 and outputs the position commands to the servo control units C1. The servo control unit C1 generates torque commands based on the position command input from the arm control unit 31a and the rotation angles detected by the encoders E1, and outputs the torque commands to the servomotors M1. As a result, the arm 60 is moved so as to comply with the operation command inputted to the remote control apparatus 2. The operations of the servo control unit C2, the encoders E2, and the servomotors M2 are the same as the operations of the servo control unit C1, the encoders E1, and the servomotors M1. The operations of the servo control unit C3, the encoder E3, and the servomotor M3 are the same as the operations of the servo control unit C1, the encoder E1, and the servomotor M1.

The arm control unit 31a is configured to operate the arm 60 based on an input signal from the operation unit 80. Specifically, the arm control unit 31a generates position commands based on the input signal (operation command) input from the operation unit 80 and the rotation angles detected by the encoders E1 or E3, and outputs the position commands to the servo control units C1 or C3. The servo control units C1 or C3 generate torque commands based on the position command input from the arm control unit 31a and the rotation angles detected by the encoders E1 or E3, and outputs the generated torque commands to the servomotors M1 or M3. As a result, the arm 60 is moved so as to follow the operation command inputted to the operation unit 80.

As illustrated in FIG. 15, the servo control units C4 that control the servomotors M4 for moving the positioner 40 is electrically connected to the positioner control unit 31b. The encoders E4 that detects the rotation angles of the servomotors M4 are electrically connected to the servo control units C4. The servo control units C5 that control the servomotors 5 for driving the front wheel (not illustrated) of the medical trolley 3 are electrically connected to the positioner control unit 31b. The encoders E5 that detects the rotation angles of the servomotors M5 are electrically connected to the servo control units C5.

An operation command is input from the input device 33 to the positioner control unit 31b. The positioner control unit 31b generates position commands based on the operation command inputted from the input device 33 and the rotation angle detected by the encoder E4, and outputs the position commands to the servo control units C4. The servo control unit C4 generates torque commands based on the position command input from the positioner control unit 31b and the rotation angles detected by the encoders E4, and outputs the torque commands to the servomotors M4. As a result, the positioner 40 is moved so as to follow the operation command input to the input device 33. Similarly, although detailed explanation is omitted, the positioner control unit 31b moves the medical trolley 3 based on the operation command input from the operation handle 34.

In a first embodiment, the control unit 31 controls the rotation amounts of the servomotor 712c1 and the servomotor 712d1 such that the opening angle between the first jaw member 430a and the second jaw member 430b corresponds to the operating angle that is received by the manipulator arm 21 for opening and closing the first jaw member 430a and the second jaw member 430b. That is, the operations of the first jaw member 430a and the second jaw member 430b are controlled by the rotation angles of the outputs of the speed reducer 712c2 of the actuator 712c and the speed reducer 712d2 of the actuator 712d. That is, the operations of the first jaw member 430a and the second jaw member 430b are controlled by the rotation angles of the rotation members 44*c* and 44*d* of the surgical instrument 4. Then, by further rotating the speed reducer 712*c*2 of the actuator 712*c* and the speed reducer 712*d*2 of the actuator 712*d* by a predetermined rotation angle from the state where the opening angle is zero degree in which the first jaw member 430*a* and the second jaw member 430*b* are closed, the opening angle between the first jaw member 430*a* and the second jaw member 430*b* becomes a desired opening angle and thus a shearing force is generated between the first jaw member 430*a* and the second jaw member 430*b*.

Here, when the shaft 420 is rotated around the rotation axis JT9 in the first direction, which is the direction to enlarge the path lengths of the first elongate element W1 and the second elongate element W2, the first elongate element W1 and the second elongate element W2 are pulled. The first direction is, for example, the JT9*a* direction. That is, only by rotating the shaft 420 in the first direction without the operation (the operating angle) of the manipulator arm 21, the first elongate element W1 and the second elongate element W2 are pulled in the direction of opening the first jaw member 430*a* and the second jaw member 430*b*. In this case, when the rotation member 44*c* winds up the first elongate element W1 and the rotation member 44*d* winds up the second elongate element W2 by the winding amounts corresponding to the operating angle of the manipulator arm 21, the opening angle between the first jaw member 430*a* and the second jaw member 430*b* exceeds a desired opening angle. Further, the amount of rotation in which the first jaw member 430*a* and the second jaw member 430*b* are rotated only by the rotation of the shaft 420 in the first direction increases as the rotation angle of the shaft 420 increases.

Further, when the shaft 420 rotates around the rotation axis JT9 in the second direction to shorten the path lengths of the first elongate element W1 and the second elongate element W2, the first elongate element W1 and the second elongate element W2 are loosened. The second direction is, for example, the JT9*b* direction. Therefore, even if the rotation member 44*c* winds up the first elongate element W1 and the rotation member 44*d* winds up the second elongate element W2 by the winding amounts corresponding to the operating angle of the manipulator arm 21, the opening angle between the first jaw member 430*a* and the second jaw member 430*b* becomes insufficient with respect to the desired opening angle. Further, the loosen amounts (slack amounts) of the first elongate element W1 and the second elongate element W2 due to the rotation of the shaft 420 in the second direction increases as the rotation angle of the shaft 420 increases.

Figure 16:
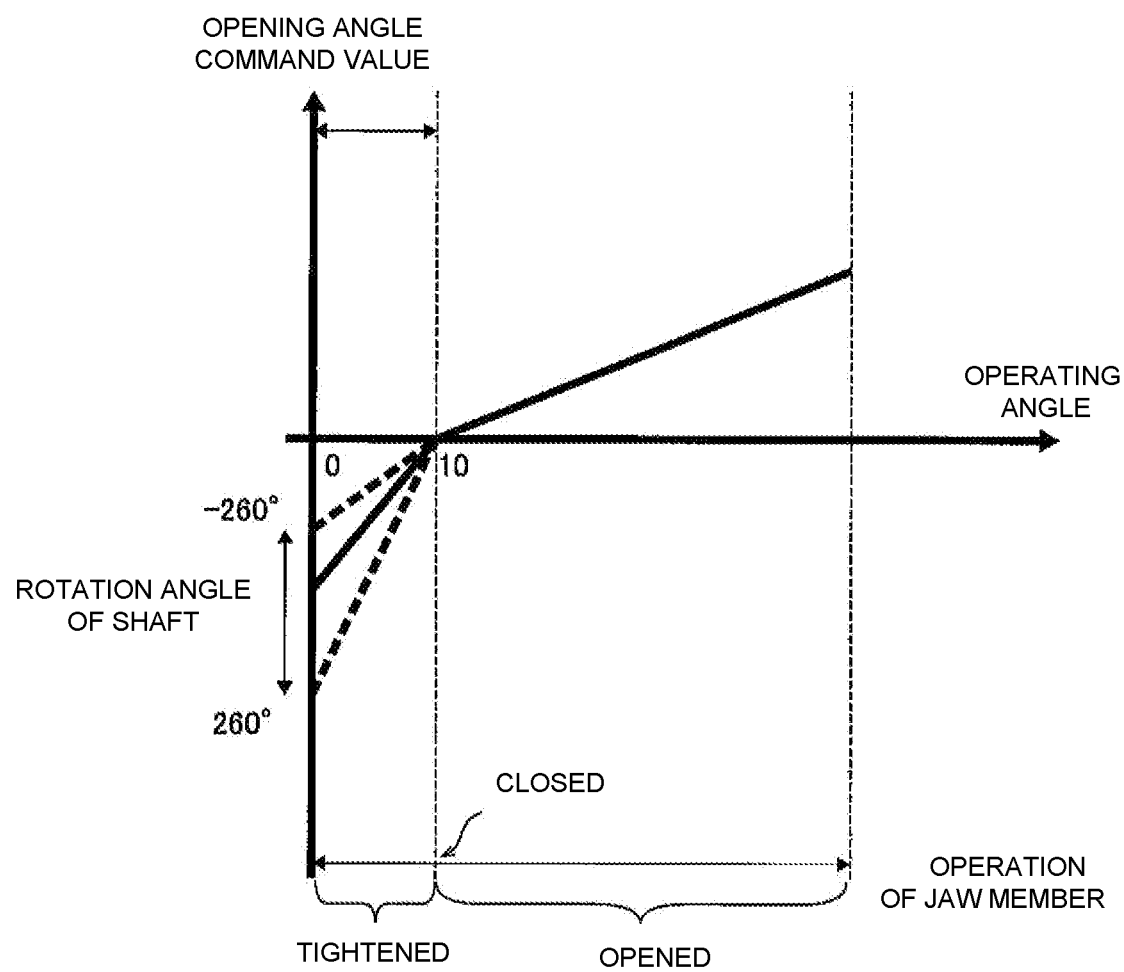
FIG. 16 is a diagram illustrating a relationship between an operating angle received by the manipulator arm and correction of a rotation amount of a servomotor according to a first embodiment.

Therefore, in a first embodiment, as illustrated in FIG. 16, the control unit 31 controls the correction amounts of the rotation amounts of the servomotor 712*c*1 and the servomotor 712*d*1 such that the correction amounts are zero when the operating angle is a threshold which corresponds to a state where the opening angle between the first jaw member 430*a* and the second jaw member 430*b* is zero whereas the absolute values of the correction amounts are increased as the operating angle deviates from the threshold and as the rotation angle of the shaft 420 increases. The operating angle accepted by the manipulator arm 21 is an angle between the pair of grip members 21*f* of the manipulator arm 21 as described above.

Further, in a first embodiment, when at least the first jaw member 430*a* and the second jaw member 430*b* are closed, the control unit 31 corrects, according to the amount of rotation of the servomotor 712*a*1 of the actuator 712*a* that rotates the shaft 420, the rotation angles of the rotation member 44*c* that drives the first elongate element W1 and the rotation member 44*d* that drives the second elongate element W2. That is, by correcting the rotation amounts of the servomotors 712*c*1 and 712*d*1, the rotation angles of the rotation members 44*c* and 44*d* are corrected.

Further, in a first embodiment, the control unit 31 corrects the rotation amounts of the servomotor 712*c*1 and the servomotor 712*d*1 only when the operating angle is smaller than the threshold. For example, the threshold of the operating angle is 10 degrees.

Specifically, in a first embodiment, when the shaft 420 rotates around the rotation axis JT9 in the first direction in which the path lengths of the first elongate element W1 and the second elongate element W2 become longer, the control unit 31 corrects the rotation angles of the servomotors 712*c*1 and 712*d*1 to reduce the winding amount of the first elongate element W1 by the rotation member 44*c* and the winding amount of the second elongate element W2 by the rotation member 44*d* depending on the rotation angle of the shaft 420 about the rotation axis JT9. Further, the amount of reduction in the winding amount of the first elongate element W1 by the rotation member 44*c* and the amount of reduction in the winding amount of the second elongate element W2 by the rotation member 44*d* are increased as the rotation angle of the shaft 420 in the first direction increases.

For example, the shaft 420 rotates in a range between −260 degrees and 260 degrees. In FIG. 16, the command value, for the servomotors 712*c*1 and 712*d*1, of the opening angle between the first jaw member 430*a* and the second jaw member 430*b* when the rotation amounts of the servomotors 712*c*1 and 712*d*1 are not corrected is illustrated by a solid line. Further, in FIG. 16, the command value, for the servomotors 712*c*1 and 712*d*1, of the opening angle between the first jaw member 430*a* and the second jaw member 430*b* when the rotation angle of the shaft 420 is rotated by −260 degrees in the first direction (the negative direction) is illustrated by an upper one of the dotted lines. In this way, an absolute value of the command value (indicated by the upper dotted line) of the opening angle between the first jaw member 430*a* and the second jaw member 430*b* when the shaft 420 is rotated in the negative direction is smaller than the absolute value of the command value (indicated by the solid line) of the opening angle when the rotation amounts are not corrected. As a result, it is possible to prevent the first jaw member 430*a* and the second jaw member 430*b* from rotating excessively. The command value of the opening angle means a command value of the rotation amount given to the servomotors 712*c*1 and 712*d*1 by the control unit 31 so that the opening angle between the first jaw member 430*a* and the second jaw member 430*b* corresponds to the operating angle, which is the angle between the grip members 21*f* of the manipulator arm 21.

Further, in a first embodiment, when the shaft 420 is rotated around the rotation axis JT9 in the second direction, opposite to the first direction, to shorten the path lengths of the first elongate element W1 and the second elongate element W2, so as to loosen the first elongate element W1 and the second elongate element W2, the control unit 31 corrects the rotation amounts of the servomotors 712*c*1 and 712*d*1 to increase the winding amount of the first elongate element W1 by the rotation member 44*c* and the winding amount of the second elongate element W2 by the rotation member 44*d* depending on the rotation angle of the shaft 20 around the rotation axis JT9. Further, the amount of increase in the winding amount of the first elongate element W1 by the rotation member 44*c* and the amount of increase in the winding amount of the second elongate element W2 by the rotation member 44*d* are increased as the rotation angle of the shaft 420 in the second direction increases.

Further, the command value of the opening angle between the first jaw member 430*a* and the second jaw member 430*b* when the rotation angle of the shaft 420 is rotated by 260 degrees in the second direction as the positive direction is illustrated by a lower one of the dotted lines in FIG. 16. In this way, the command value of the opening angle between the first jaw member 430*a* and the second jaw member 430*b* when the shaft 420 is rotated in the positive direction is larger in the negative direction than the command value of the opening angle when the rotation amounts are not corrected (indicated by the solid line). That is, the absolute value of the command value of the opening angle between the first jaw member 430*a* and the second jaw member 430*b* when the shaft 420 is rotated in the positive direction is larger than the absolute value of the command value of the opening angle when the rotation amounts are not corrected (indicated by the solid line). As a result, it is possible to appropriately generate the shearing force between the first jaw member 430*a* and the second jaw member 430*b*.

Further, when the operating angle for opening and closing the first jaw member 430*a* and the second jaw member 430*b* is greater than the threshold, the rotation amounts of the servomotor 712*c*1 configured to drive the first jaw member 430*a* and the servomotor 712*d*1 configured to drive the second jaw member 430*b* are not corrected. Here, since the end effector 430 is a pair of scissors in a first embodiment as described above, the first jaw member 430*a* and the second jaw member 430*b* are rubbed together to cut (shear) the object. As illustrated by the dashed line in FIG. 19, if the rotation amounts of the servomotors 712*c*1 and 712*d*1 are corrected, when the operating angle is greater than the threshold (when shifting from the closed state to the open state of the first jaw member 430*a* and the second jaw member 430*b*) so as to reduce the winding amount of the first elongate element W1 by the rotation member 44*c* and the winding amount of the second elongate element W2 by the rotation member 44*d* according to the rotation angle of the shaft 420 in the first direction in the same manner as the operating angle is not greater than the threshold, it may become difficult to open the first jaw member 430*a* and the second jaw member 430*b* since the first jaw member 430*a* and the second jaw member 430*b* are rubbed against each other. Therefore, in a first embodiment, the rotation amounts of the servomotors 712*c*1 and 712*d*1 are corrected only when the opening angle between the first jaw member 430*a* and the second jaw member 430*b* are equal to or less than zero degrees corresponding to the threshold. Note that, in a gripping type end effector as in a second embodiment described below, the problem that the first jaw member 430*a* and the second jaw member 430*b* are difficult to open does not occur.

Further, the upper dotted line in FIG. 16 indicates the command value of the opening angle when the shaft 420 is rotated by −260 degrees, whereas the lower dotted line in FIG. 16 indicates the command value of the opening angle when the shaft 420 is rotated by 260 degrees. The inclinations of the dotted lines representing the command value of the opening angle changes according to the rotation angle of the shaft 420. When the operating angle is equal to the threshold, the command value of the opening angle is zero regardless of the rotation angle of the shaft 420. That is, the command value of the opening angle starts from zero and increases in the absolute value according to the operating angle and the rotation angle of the shaft.

Further, in a first embodiment, as illustrated in FIG. 9, the surgical instrument 4 includes a storage 444 (or a memory) that stores therein information on the type of the surgical instrument 4. The control unit 31 corrects the rotation amounts of the actuators 712*c* and 712*d* based on the information stored in the storage 444. The storage 444 is provided in the housing 410 of the surgical instrument 4. Further, a connector 445 is provided on the lower surface of the surgical instrument 4, which is the side to be connected to the adaptor 500. In the state where the surgical instrument 4 is attached to the adaptor 500, the information stored in the storage 444 is transmitted to the control unit 31 via the connector 445. For example, the command value of the opening angle between the two jaw members are indicated by the dotted line in FIG. 16, which illustrates the inclination of the command value is different for each type of the surgical instrument 4. The control unit 31 corrects the rotation amounts of the servomotors 712*c*1 and 712*d*1 based on the information stored in the storage 444, that is, based on the inclination of the command value of the opening angle depending on the type of the surgical instrument 4.

Figure 17:
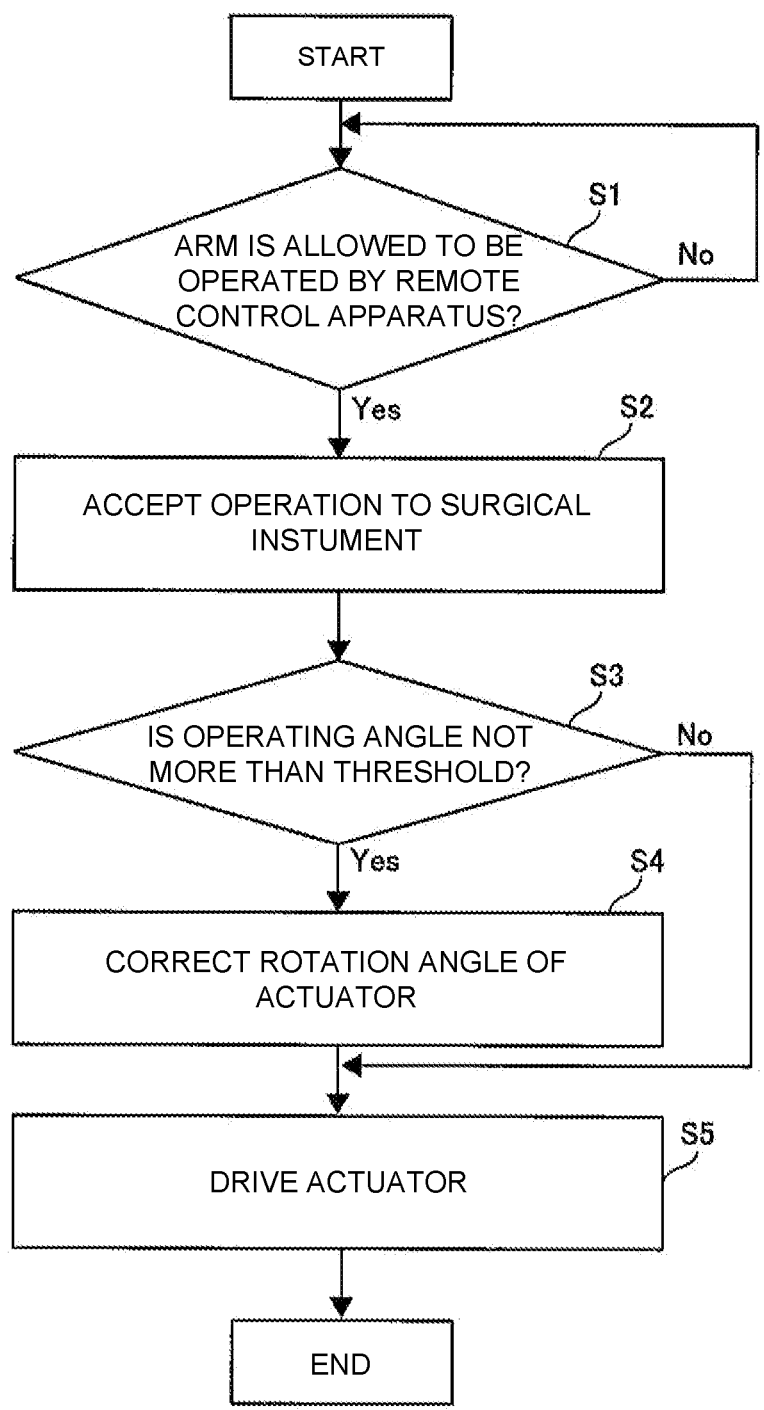
FIG. 17 is a diagram illustrating a view of a control flow of the control unit according to a first embodiment.

Next, with reference to FIG. 17, a control method of the surgical system 100 is described below.

First, in step S1, the control unit 31 determines whether or not the arm 60 of the medical manipulator 1 is allowed to be operated by the remote control apparatus 2. When grip members 21*f* are operated while a sensor(s) provided in the vicinity of the monitor 24 detects the head of the operator, the control unit 31 determines that the arms 60 are allowed to be operated by the remote control apparatus 2. In the case of "Yes" in step S1, the process proceeds to step S2. The operation of step S1 is repeated until it is determined that the arm 60 of the medical manipulator 1 is allowed to be operated by the remote control apparatus 2.

Next, in step S2, the control unit 31 receives an operation of the manipulator arm(s) 21 of the remote control apparatus 2 to operate the surgical instrument 4. That is, the control unit 31 accepts an operation for rotating the shaft 420 about the rotation axis JT9 and an operation for opening and closing the first jaw member 430*a* and the second jaw member 430*b*.

Next, in steps S3 and S4, when the first jaw member 430*a* and the second jaw member 430*b* are closed, the control unit 31 corrects the rotation amounts of the servomotor 712*c*1 for driving the first jaw member 430*a* and the servomotor 712*d*1 for driving the second jaw member 430*b*, according to the operating angle, the rotation angle, and the rotation direction of the shaft 420 about the rotation axis JT9. Specifically, in step S3, the control unit 31 determines whether or not the operating angle is equal to or less than the threshold. In the case of "yes" in step S3, the process proceeds to step S4. In step S4, when the shaft 420 is rotated in the first direction, the control unit 31 corrects the rotation amounts of the servomotor 712*c*1 for driving the first jaw member 430*a* and the servomotor 712*d*1 for driving the second jaw member 430*b* to be decreased according to the operating angle and the rotation angle of the shaft 420 about the rotation axis JT9. In step S4, when the shaft 420 rotates in the second direction, the control unit 31 corrects the rotation amounts of the servomotor 712*c*1 for driving the first jaw member 430*a* and the servomotor 712*d*1 for driving the second jaw member 430*b* to be increased according to the operating angle and the rotation angle of the shaft 420 about the rotation axis JT9. Then, in step S5, the control unit 31 drives the servomotors 712*c*1 and 712*d*1 according to the corrected rotation amounts.

In the case of "No" in step S3, the process proceeds to step S5. That is, the control unit 31 drives the servomotors 712c1 and 712d1 without correcting the rotation amounts of the servomotors 712c1 and 712d1.

Steps S1 to S5 described above are performed for each of the arms 60 corresponding to the two manipulator arms 21.

Effects of First Embodiment

In a first embodiment, the following effects can be obtained.

In a first embodiment, as described above, the control unit 31 controls the rotation amounts of the servomotor 712c1 and the servomotor 712d1 such that the opening angles of the first jaw member 430a and the second jaw member 430b corresponds to the operating angle for opening and closing the first jaw member 430a and the second jaw member 430b received by the manipulator arm 21. With this configuration, even when the path lengths of the first elongate element W1 and the second elongate element W2 are changed due to the rotation of the shaft 420, the rotation amounts of the servomotor 712c1 configured to drive the first jaw member 430a and the servomotor 712d1 configured to drive the second jaw member 430b are corrected, so that the opening angle between the first jaw member 430a and the second jaw member 430b becomes the desired opening angle. Therefore, even when the path lengths of the first elongate element W1 and the second elongate element W2 change, it is possible to reduce the change in the shearing force generated between the first jaw member 430a and the second jaw member 430b.

Further, in a first embodiment, as described above, the first elongate element W1 and the second elongate element W2 are arranged between the rotation members 44c and 44d and the first and second jaw members 430a and 430b in a manner that the first elongate element W1 and the second elongate element W2 are twisted in the shaft 420 with respect to the rotation axis JT9 of the shaft 420. Here, in the case where the first elongate element W1 and the second elongate element W2 are twisted with respect to the rotation axis JT9 of the shaft 420 in the shaft 420, the path lengths of the first elongate element W1 and the second elongate element W2 in the shaft 420 become longer when the shaft 420 is rotated in the first direction whereas the path lengths of the first elongate element W1 and the second elongate element W2 in the shaft 420 become shorter when the shaft 420 is rotated in the second direction. In view of this, the control unit 31 corrects, when the shaft 420 is rotated in the first direction, the rotation amounts of the servomotor 712c1 for driving the first jaw member 430a and the servomotor 712d1 for driving the second jaw member 430b to be reduced and correct, when the shaft 420 is rotated in the second direction, the rotation amounts of the servomotor 712c1 for driving the first jaw member 430a and the servomotor 712d1 for driving the second jaw member 430b to be increased, so as to reduce the change in the shearing force generated between the two jaw members 430a and 430b.

Further, in a first embodiment, as described above, the control unit 31 corrects the rotation amount of the servomotor 712c1 and the servomotor 712d1 only when the operating angle that is received by the manipulator arm 21 for opening and closing the first jaw member 430a and the second jaw member 430b is not more than the threshold which corresponds to the state where the opening angle between the first jaw member 430a and the second jaw member 430b is zero degree. Accordingly, the difficulty to open the first jaw member 430a and the second jaw member 430b can be reduced.

Further, in a first embodiment, when the shaft 420 is rotated around the rotation axis JT9 in the first direction to enlarge the path lengths of the first elongate element W1 and the second elongate element W2, the control unit 31 corrects the rotation angles of the servomotors 712c1 and 712d1 to reduce the winding amount of the first elongate element W1 by the rotation member 44c and the winding amount of the second elongate element W2 by the rotation member 44d, as described above. Accordingly, since the first elongate element W1 and the second elongate element W2 are pulled when the shaft 420 is rotated around the rotation axis JT9 in the first direction, the opening angle between the first jaw member 430a and the second jaw member 430b is adjusted to the desired opening angle, by reducing the winding amount of the first elongate element W1 by the rotation member 44c and the second elongate element W2 by the rotation member 44d.

In a first embodiment, as described above, the reduced amount of the winding amount of the first elongate element W1 by the rotation member 44c and the reduced amount of the winding amount of the second elongate element W2 by the rotation member 44d are zero when the operating angle is the threshold and increase starting from zero as the operating angle decreases from the threshold and as the rotation angle of the shaft 420 in the first direction increases. With this configuration, even if the path lengths of the first elongate element W1 and the second elongate element W2 are changed along with change of the rotation angle of the shaft 420, the opening angle between the first jaw member 430a and the second jaw member 430b is controlled to be the desired opening angle.

Further, in a first embodiment, when the shaft 420 is rotated around the rotation axis JT9 in the second direction, which is opposite to the first direction, that shortens the path lengths of the first elongate element W1 and the second elongate element W2, the control unit 31 corrects the rotation angles of the servomotors 712c1 and 712d1 to increase the winding amount of the first elongate element W1 by the rotation member 44c and the winding amount of the second elongate element W2 by the rotation member 44d, as described above. Accordingly, since the first elongate element W1 and the second elongate element W2 loosen when the shaft 420 is rotated around the rotation axis JT9 in the second direction, the opening angle between the first jaw member 430a and the second jaw member 430b is adjusted to the desired opening angle by increasing the winding amount of the first elongate element W1 by the rotation member 44c and the winding amount of the second elongate element W2 by the rotation member 44d.

In a first embodiment, as described above, the increased amount of the winding amount of the first elongate element W1 by the rotation member 44c and the increased amount of the winding amount of the second elongate element W2 by the rotation member 44d are zero when the operating angle is the threshold and increase as the operating angle decreases from the threshold and as the rotation angle of the shaft 420 in the second direction increases. With this configuration, even if the path lengths of the first elongate element W1 and the second elongate element W2 are changed along with change of the rotation angle of the shaft 420, the opening angle between the first jaw member 430a and the second jaw member 430b is controlled to be the desired opening angle.

Further, in a first embodiment, as described above, the control unit 31 is configured to correct the rotation amounts of the servomotors 712c1 and 712d1 based on the information of the surgical instrument 4 stored in the storage 444. Accordingly, the control unit 31 can appropriately control the opening angle between the first jaw member 430a and the second jaw member 430b to the desired opening angle by referring to the information of the type of the surgical instrument 4 stored in the storage 444.

Second Embodiment

Next, a medical manipulator 700 according to a second embodiment is described with reference to FIGS. 18 and 19. In a second embodiment, an end effector of a grip type is provided at a distal end of a surgical instrument 730.

Figure 18:
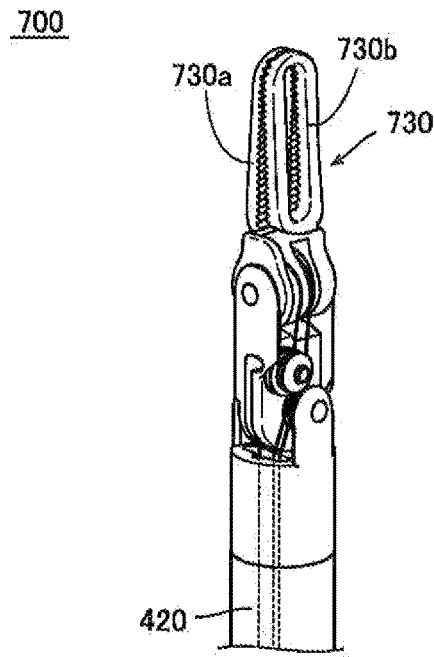
FIG. 18 is a diagram illustrating a perspective view of an end effector of a surgical instrument according to a second embodiment.

As illustrated in FIG. 18, in the medical manipulator 700, a first jaw member 730a and a second jaw member 730b of the surgical instrument 730 constitute a gripping type end effector configured to grip an object. A gripping force between the first jaw member 730a and the second jaw member 730b is generated by further rotating the rotation member 44c in the C2 direction and the rotation member 44d in the C4 direction by predetermined angles after the end effector members 430a and 430b are closed. The gripping end effector is, for example, graspers.

Figure 19:
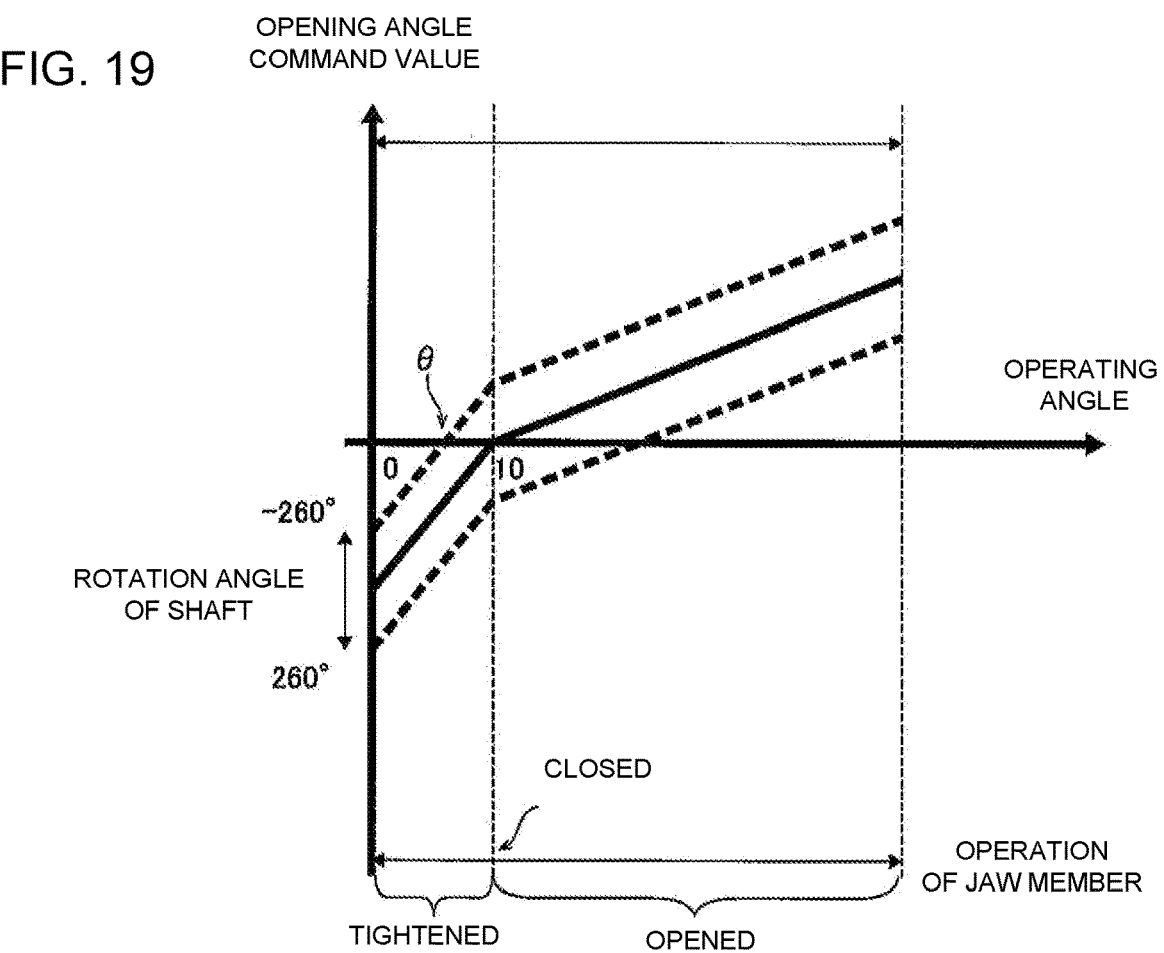
FIG. 19 is a diagram illustrating a relationship between an operating angle received by a manipulator arm and correction of rotation amount of a servomotor according to a second embodiment.

Here, in a second embodiment, as shown in FIG. 19, the control unit 31 corrects the rotation amounts of the servomotors 712c1 and 712d1 according to the rotation angle of the shaft 420 about the rotation axis JT9 regardless of the operating angle of the manipulator arm 21. That is, the control unit 31 corrects the rotation amounts of the servomotors 712c1 and 712d1 according to the rotation angle of the shaft 420 regardless of whether the first jaw member 730a and the second jaw member 730b are closed or not. Further, the control unit 31 set the rotation amounts of the servomotors 712c1 and 712d1 to rotation amounts that are offset (corrected) according to the rotation angle of the shaft 420 about the rotation axis JT9 of the shaft 420.

Specifically, when the shaft 420 rotates about the rotation axis JT9 in the first direction so as to enlarge the path lengths of the first elongate element W1 and the second elongate element W2, the control unit 31 corrects the rotation amounts of the servomotors 712c1 and 712d1 to reduce the winding amount of the first elongate element W1 by the rotation member 44c and the winding amount of the second elongate element W2 by the rotation member 44d according to the rotation angle of the shaft 20. Also, when the shaft 420 rotates about the rotation axis JT9 in the second direction, which is opposite to the first direction, so as to shorten the path lengths of the first elongate element W1 and the second elongate element W2, the control unit 31 corrects the rotation amounts of the servomotors 712c1 and 712d1 to increase the winding amount of the first elongate element W1 of the rotation member 44c and the winding amount of the second elongate element W2 of the rotation member 44d according to the rotation angle of the shaft 20. Note that the magnitude of the correction amounts changes according to the rotation angle of the shaft 420 but does not depend on the operating angle of the manipulator arm 21.

For example, the shaft 420 rotates in a range between −260 degrees and 260 degrees. In FIG. 19, the command value of the opening angle between the first jaw member 430a and the second jaw member 430b when the rotation amounts of the servomotors 712c1 and 712d1 are not corrected is illustrated by a solid line. Further, the command value of the opening angle between the first jaw member 430a and the second jaw member 430b, when the rotation angle of the shaft 420 is rotated by −260 degrees in the first direction as the negative direction, is illustrated by an upper one of the dotted lines in FIG. 19.

As illustrated in FIG. 19, when the shaft 420 is rotated in the negative diction, the command value of the opening angle between the first jaw member 430a and the second jaw member 430b is corrected to be smaller in the negative direction than the command value of the opening angle in the case where the rotation amounts are not corrected. With this configuration, in the case where the operating angle is not more than 8 which is less than 10 degrees, the absolute value of the corrected command value (indicated by the upper dotted line in FIG. 19) of the opening angle between the first jaw member 430a and the second jaw member 430b when the shaft 420 is rotated in the negative diction is smaller than the absolute value of the uncorrected command value (indicated by the solid line in FIG. 19). Accordingly, it is possible to suppress generating a excessive gripping force by the first jaw member 430a and the second jaw member 430b in the case where the operating angle is not more than 8 which is less than 10 degrees.

Further, the command value of the opening angle between the first jaw member 430a and the second jaw member 430b when the rotation angle of the shaft 420 is rotated by 260 degrees in the second direction (the positive direction) is illustrated by a lower one of the dotted lines in FIG. 19. When the operating angle is 10 degrees or less, the command value of the opening angle indicated by the lower dotted line in FIG. 19 is corrected to be larger in the negative direction than the command value of the uncorrected opening angle indicated by the solid line in FIG. 19. In other words, when the operating angle is 10 degrees or less, the absolute value of the corrected command value of the opening angle indicated by the lower dotted line in FIG. 19 is larger than the absolute value of the command value of the uncorrected opening angle indicated by the solid line in FIG. 19. As a result, it is possible to appropriately generate the gripping force between the first jaw member 430a and the second jaw member 430b. Note that in the case of the gripping type end effector, the first jaw member 430a and the second jaw member 430b are arranged so as not to be rubbed against each other like scissors. Therefore, the problem of difficulty in opening the first jaw member 430a and the second jaw member 430b does not occur.

Effects of Second Embodiment

In a second embodiment, the following effects can be obtained.

In a second embodiment, as described above, the control unit 31 set the rotation amounts of the actuators 712c and 712d to the rotation amounts that are corrected (offset) according to the rotation angle of the shaft 420 about the rotation axis JT9 of the shaft 420. With this configuration, by simply correcting the rotation amounts of the servomotors 712c1 and 712d1 according to the rotation angle of the shaft 420 about the rotation axis JT9, the command value of the opening angle can be easily corrected. Therefore, it is possible to reduce the burden on the control unit 31.

Further in a second embodiment, as described above, the control unit 31 is configured, when the shaft 420 rotates about the rotation axis JT9 in the first direction, to correct the rotation amounts of the servomotors 712c1 and 712d1 according to the rotation angle of the shaft 20 so as to reduce the winding amount of the first elongate element W1 by the rotation member 44c and the winding amount of the second elongate element W2 by the rotation member 44d, and is configured, when the shaft 420 rotates about the rotation axis JT9 in the second direction, to correct the rotation amounts of the servomotors 712c1 and 712d1 according to the rotation angle of the shaft 20 so as to increase the winding amount of the first elongate element W1 by the rotation member 44c and the winding amount of the second elongate element W2 by the rotation member 44d. With this configuration, even in both cases where the path lengths of the first elongate element W1 and the second elongate element W2 becomes longer so that the first elongate element W1 and the second elongate element W2 are tighten and where the path lengths becomes shorter so that the first elongate element W1 and the second elongate element W2 are loosen, the opening angle between the first jaw member 430a and the second jaw member 430b can be adjusted to the desired opening angle.

Further, in a second embodiment, the offset amounts (the corrected amounts) of the winding amount of the first elongate element W1 by the rotation member 44c and the winding amount of the second elongate element W2 by the rotation member 44d increase as the rotation angle of the shaft 420 in the first direction increases and increase as the rotation angle of the shaft 420 in the second direction increases, as described above.

Modifications

Note that one or more embodiments disclosed herein should be considered as exemplary in all respects and do not limit the invention. The scope of the invention is defined not by the above-described one or more embodiments, but by the scope of claims, and includes all modifications (variations) within equivalent meaning and scope to those of the claims.

Further, in first and second embodiments described above, the case has been described in which the control unit 31 is provided in the medical manipulator 1. However, the disclosure is not limited thereto. For example, the control unit 31 may be provided in the remote control apparatus 2. Further, the control unit 31 may be provided separately from the medical manipulator 1 and the remote control apparatus 2.

Figure 20:
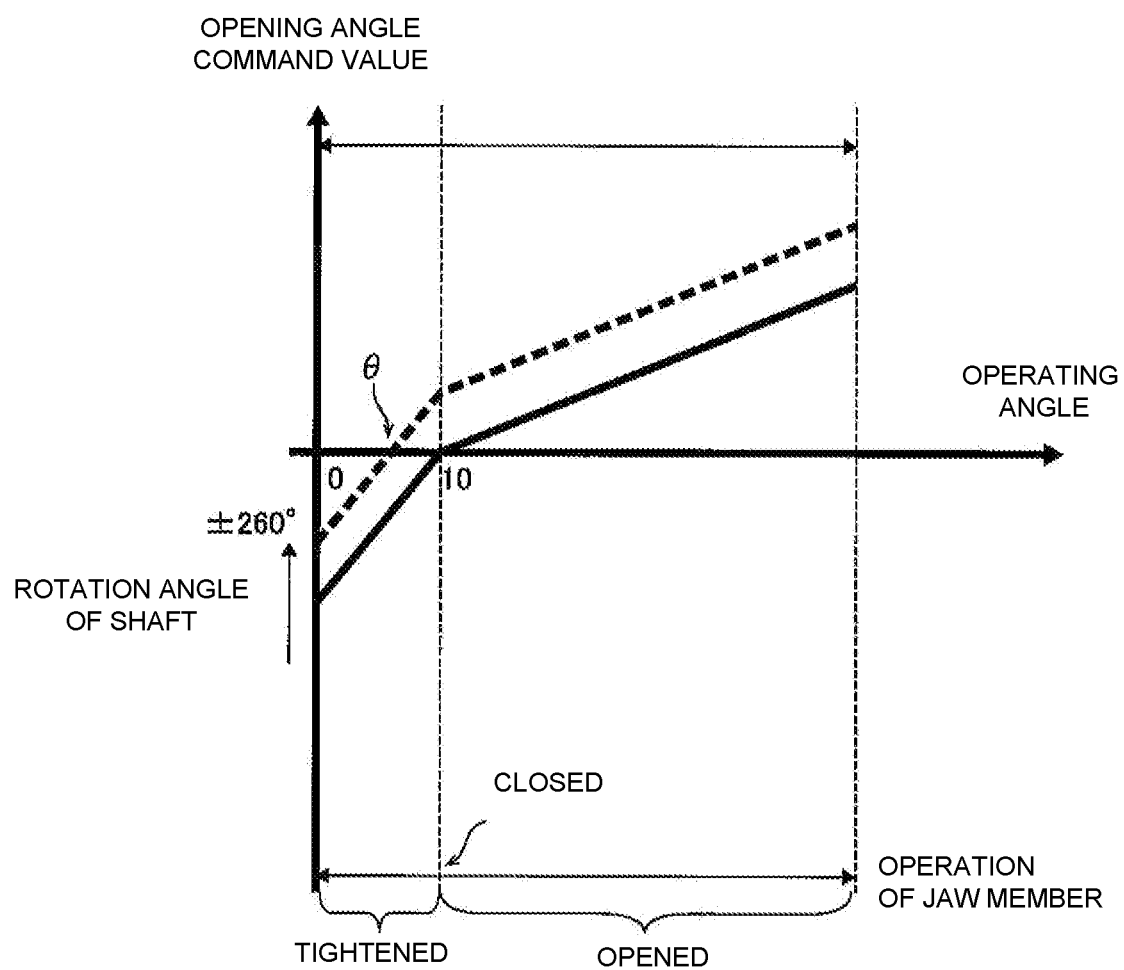
FIG. 20 is a diagram illustrating a relationship between an operating angle received by a manipulator arm and correction of a rotation amount of a servomotor according to a first modification.
Figure 21:
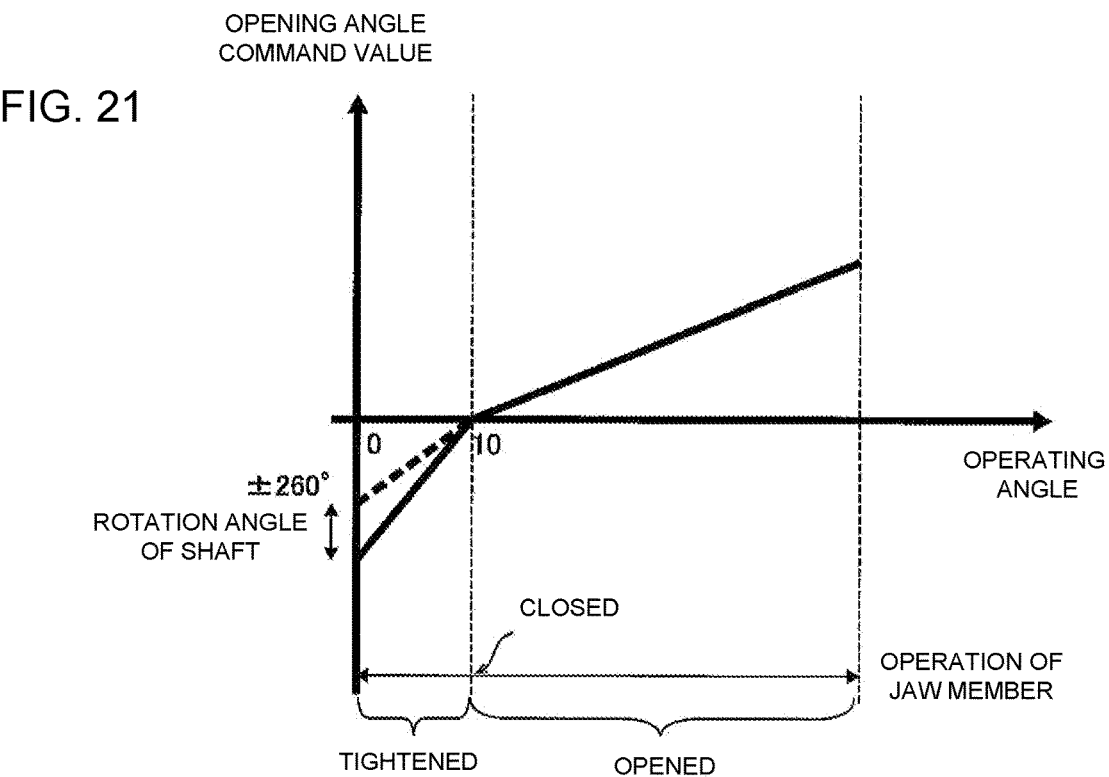
FIG. 21 is a diagram illustrating a relationship between an operating angle received by a manipulator arm and correction of a rotation amount of a servomotor according to a second modification.

Further, in first and second embodiments described above, the case has been described in which in the state where the rotation angle of the shaft 20 is zero, the first elongate element W1 and the second elongate element W2 between the rotation members 44c and 44d and the first and second jaw members 430a and 430b are twisted 180 degrees about the rotation axis JT9 of the shaft 420. However, the disclosure is not limited thereto. For example, as illustrated in FIG. 11, in the state where the rotation angle of the shaft 420 is zero, the first elongate element W1 and the second elongate element W2 may not be twisted with respect to the rotation axis JT9 of the shaft 420 in the shaft 420. In a case where the first jaw member 430a and the second jaw member 430b are configured as a gripping type end effector, the rotation amounts of the servomotors 712c1 and 712d1 are corrected according to the rotation angle of the shaft 420 so as to reduce the winding amount of the first elongate element W1 around the rotation member 44c and the winding amount of the second elongate element W2 around the rotation member 44d, regardless of whether the shaft 420 is rotated in the first direction or the second direction, as illustrated in FIG. 20. In a case where the first jaw member 430a and the second jaw member 430b are configured as scissors, the rotation amounts of the servomotors 712c1 and 712d1 are not corrected when the operating angle exceeds the threshold as illustrated in FIG. 21.

Figure 22:
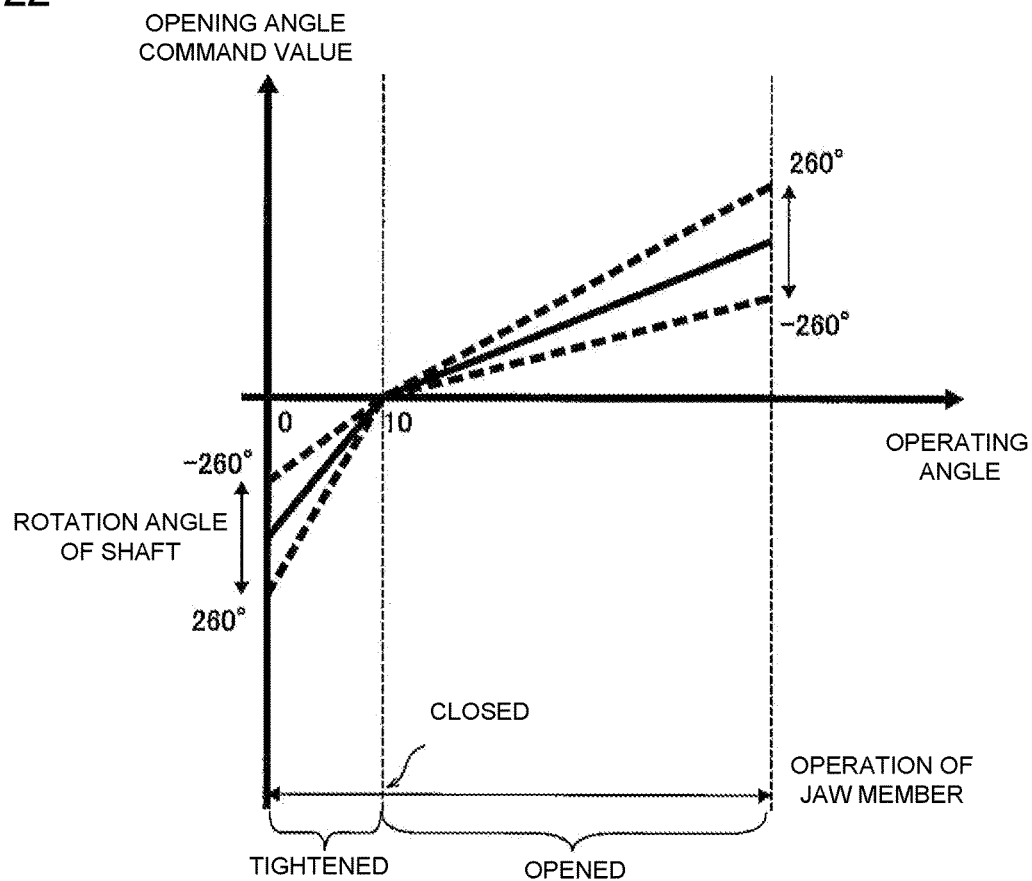
FIG. 22 is a diagram illustrating a relationship between an operating angle received by a manipulator arm and correction of a rotation amount of a servomotor according to a third modification.

Further, in a first embodiment described above, the case has been described in which the rotation amounts of the servomotors 712c1 and 712d1 are corrected only when the operating angle is equal to or less than the threshold. However, the disclosure is not limited thereto. For example, as illustrated in FIG. 22, even when the operating angle is larger than the threshold, the rotation amounts of the servomotors 712c1 and 712d1 may be corrected. In such a case, when the shaft 420 is rotated in the positive direction to loosen the first elongate element W1 and the second elongate element W2 in the state where the operating angle is greater than the threshold, the rotation amounts of the servomotors 712c1 and 712d1 are corrected based on the operating angle and the rotation angle of the shaft 20 to increase the winding amount of the first elongate element W1 by the rotation member 44c and the winding amount of the second elongate element W2 by the rotation member 44d. To the contrary, when the shaft 420 is rotated in the negative direction to tighten (pull) the first elongate element W1 and the second elongate element W2 in the state where the operating angle is greater than the threshold, the rotation amounts of the servomotors 712c1 and 712d1 are corrected based on the operating angle and the rotation angle of the shaft 20 to decrease the winding amount of the first elongate element W1 by the rotation member 44c and the winding amount of the second elongate element W2 by the rotation member 44d. Here, since the correction amounts of the rotation amounts are set to zero when the operating angle is the threshold and the correction amounts are increased as the operating angle increases from the threshold and as the rotation angle of the shaft 420 increases, the problem of difficulty in opening the first jaw member 430a and the second jaw member 430b does not occur.

Further, in a first embodiment described above, the case has been described in which the rotation amounts of the servomotors 712c1 and 712d1 are corrected according to the rotation angle of the shaft 420 even when the operating angle is more than the threshold. However, the disclosure is not limited thereto. For example, when the operating angle is larger than the threshold, the rotation amounts of the servomotors 712c1 and 712d1 may not be corrected.

In first and second embodiments described above, the storage 444 provided in the surgical instrument 4 stores therein the information of the type of the surgical instrument 4. However, the disclosure is not limited thereto. For example, the information on the type of the surgical instrument 4 may be input by the operator.

Further, in first and second embodiments described above, the case has been described in which the number of the arms 60 provided is four. However, the disclosure is not limited thereto. In the disclosure, the number of the arms 60 may be any number as long as at least one is provided.

Further, in first and second embodiments described above, the case has been described in which each of the arm section 61 and the positioner 40 are configured as the 7-axis articulated robot. However, the disclosure is not limited thereto. For example, each of the arm section 61 and the positioner 40 may be configured as an articulated robot other than the 7-axis articulated robot (for example, a 6-axis articulated robot, an 8-axis articulated robot, or the like).

Further, in first and second embodiments described above, the case has been described in which the medical manipulator 1 includes the medical trolley 3, the positioner 40, the arm base 50, and the arms 60. However, the disclosure is not limited thereto. For example, the medical manipulator 1 may include only the arms 60 and not include the medical trolley 3, the positioner 40, and the arm base 50.

The functions of each of the elements disclosed herein may be carried out by a circuitry or a processing circuitry including a general purpose processor, a dedicated processor, an integrated circuit, an ASIC (Application Special Integrated Circuit), a conventional circuit, or a combination of two or more of them, that is configured or programmed to perform the functions. A processor is considered a processing circuitry or a circuitry because it contains transistors and other circuit elements. In the disclosure, a circuit, a unit, or a means may be either a hardware that is configured to perform the recited function(s) or a hardware that is programmed to perform the recited function(s). The hardware may be the hardware disclosed herein, or may be other known hardware that is programmed or configured to perform the function(s) described. If the hardware is a processor which is considered as a type of a circuit, a circuit, a means, or a unit is a combination of hardware and software, and the software is used to configure the hardware and/or the processor.

The invention includes other embodiments or modifications in addition to one or more embodiments described above without departing from the spirit of the invention. The one or more embodiments described herein are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A surgical system comprising:
    a patient-side apparatus including an arm to which a surgical instrument is to be attached;
    an operator-side apparatus including an operation part configured to receive an operation for operating the surgical instrument;
    a controller configured to control an operation of the surgical instrument based on a command from the operation part, wherein
    the surgical instrument comprises:
    a shaft;
    a first jaw member and a second jaw member provided on a side of a distal end of the shaft;
    a first elongate element for operating the first jaw member; and
    a second elongate element for operating the second jaw member; wherein
    the arm includes a first drive part configured to drive the first elongate element and a second drive part configured to drive the second elongate element,
    the controller is configured to:
    control rotation amounts of the first drive part and the second drive part such that an opening angle between the first jaw member and the second jaw member corresponds to an operating angle received by the operation part for opening and closing the first jaw member and the second jaw member; and
    correct, according to a rotation angle of the shaft about a rotation axis of the shaft, the rotation amounts of the first drive part and the second drive part that correspond to the operating angle.

2. The surgical system according to claim 1, wherein
    the surgical instrument includes: a first rotation member provided on a side of a proximal end of the shaft and configured to be rotated by the first drive part so as to drive the first elongate element; and a second rotation member provided on the side of the proximal end of the shaft and configured to be rotated by the second drive part so as to drive the second elongate element,
    the first elongate element extends through an inside of the shaft and connects the first jaw member and the first rotation member, and
    the second elongate element extends through the inside of the shaft and connects the second jaw member and the second rotation member.

3. The surgical system according to claim 2, wherein
    the first elongate element comprises a first portion, a second portion and a first fixation portion provided between the first portion and the second portion, wherein the first fixation portion is fixed to the first jaw member, an end portion of the first portion is wound around the first rotation member in a first winding direction, and an end portion of the second portion is wound around the first rotation member in a second winding direction opposite to the first winding direction, and
    the second elongate element comprises a third portion, a fourth portion and a second fixation portion provided between the third portion and the fourth portion, wherein the second fixation portion is fixed to the second jaw member, an end portion of the third portion is wound around the second rotation member in the first winding direction, and an end portion of the fourth portion is wound around the second rotation member in the second winding direction.

4. The surgical system according to claim 2, wherein
    the controller is configured, when the shaft is rotated about the rotation axis of the shaft, to correct the rotation amounts of the first drive part and the second drive part according to the rotation angle of the shaft so as to reduce a winding amount of the first elongate element by the first drive part and a winding amount of the second elongate element by the second drive part.

5. The surgical system according to claim 2, wherein
    the first elongate element and the second elongate element are arranged between the first and second rotation members and the first and second jaw members such that the first elongate element and the second elongate element are twisted in the shaft with respect to the rotation axis of the shaft.

6. The surgical system according to claim 5, wherein
    the controller is configured, when the shaft is rotated about the rotation axis of the shaft in a first direction which enlarges path lengths of the first elongate element and the second elongate element, to correct the rotation amounts of the first drive part and the second drive part so as to reduce a winding amount of the first elongate element by the first drive part and a winding amount of the second elongate element by the second drive part according to the rotation angle of the shaft in the first direction, and
    the controller is configured, when the shaft is rotated about the rotation axis of the shaft in a second direction, opposite to the first direction, which shortens the path lengths of the first elongate element and the second elongate element, to correct the rotation amounts of the first drive part and the second drive part so as to increase the winding amount of the first elongate element by the first drive part and the winding amount of the second elongate element by the second drive part according to the rotation angle of the shaft in the second direction.

7. The surgical system according to claim 1, wherein
    the first jaw member and the second jaw member forms a pair of scissors configured to cut an object, and
    the controller is configured:
    when the opening angle between the first jaw member and the second jaw member is zero degree, which corresponds to a threshold, to set correction amounts of the rotation amounts of the first drive part and the second drive part to zero, and to increase absolute values of the correction amounts of the rotation amounts of the first drive part and the second drive part, as the operating angle deviates from the threshold and as the rotation angle of the shaft increases.

8. The surgical system according to claim 7, wherein the controller is configured to correct the rotation amounts of the first drive part and the second drive part only when the operating angle is less than the threshold.

9. The surgical system according to claim 1, wherein the first jaw member and the second jaw member form a gripping type end effector configured to grip an object.

10. The surgical system according to claim 9, wherein the controller is configured to correct, according to the rotation angle of the shaft about the rotation axis of the shaft, the rotation amounts of the first drive part and the second drive part.

11. The surgical system according to claim 1, wherein the surgical instrument comprises a storage that stores therein information of a type of the surgical instrument, and the controller is configured to correct the rotation amounts of the first drive part and the second drive part based on the information of the type of the surgical instrument stored in the storage.

12. A controller for controlling a surgical system that comprises a patient-side apparatus including an arm to which a surgical instrument is to be attached and an operator-side apparatus including an operation part configured to receive an operation for operating the surgical instrument, wherein the controller is configured to control an operation of the surgical instrument based on a command from the operation part, wherein the surgical instrument comprises: a shaft; a first jaw member and a second jaw member provided on a side of a distal end of the shaft; a first elongate element for operating the first jaw member; and a second elongate element for operating the second jaw member, wherein the arm includes a first drive part configured to drive the first elongate element and a second drive part configured to drive the second elongate element, wherein the controller is configured to control rotation amounts of the first drive part and the second drive part such that an opening angle between the first jaw member and the second jaw member corresponds to an operating angle received by the operation part for opening and closing the first jaw member and the second jaw member, and the controller is configured to:

receive, from the operation part, the operating angle for opening and closing the first jaw member and the second jaw member; and correct, according to a rotation angle of the shaft about a rotation axis of the shaft, the rotation amounts of the first drive part and the second drive part that correspond to the operating angle.

13. The controller according to claim 12, wherein the surgical instrument includes: a first rotation member provided on a side of a proximal end of the shaft and configured to be rotated by the first drive part so as to drive the first elongate element; and a second rotation member provided on the side of the proximal end of the shaft and configured to be rotated by the second drive part so as to drive the second elongate element, the first elongate element extends through an inside of the shaft and connects the first jaw member and the first rotation member, and the second elongate element extends through the inside of the shaft and connects the second jaw member and the second rotation member.

14. The controller according to claim 13, wherein the first elongate element comprises a first portion, a second portion and a first fixation portion provided between the first portion and the second portion, wherein the first fixation portion is fixed to the first jaw member, an end portion of the first portion is wound around the first rotation member in a first winding direction, and an end portion of the second portion is wound around the first rotation member in a second winding direction opposite to the first winding direction, and the second elongate element comprises a third portion, a fourth portion and a second fixation portion provided between the third portion and the fourth portion, wherein the second fixation portion is fixed to the second jaw member, an end portion of the third portion is wound around the second rotation member in the first winding direction, and an end portion of the fourth portion is wound around the second rotation member in the second winding direction.

15. The controller according to claim 13, wherein the controller is configured, when the shaft is rotated about the rotation axis of the shaft, to correct the rotation amounts of the first drive part and the second drive part according to the rotation angle of the shaft so as to reduce a winding amount of the first elongate element by the first drive part and a winding amount of the second elongate element by the second drive part.

16. The controller according to claim 13, wherein the first elongate element and the second elongate element are arranged between the first and second rotation members and the first and second jaw members such that the first elongate element and the second elongate element are twisted in the shaft with respect to the rotation axis of the shaft.

17. The controller according to claim 16, wherein the controller is configured, when the shaft is rotated about the rotation axis of the shaft in a first direction which enlarges path lengths of the first elongate element and the second elongate element, to correct the rotation amounts of the first drive part and the second drive part so as to reduce a winding amount of the first elongate element by the first drive part and a winding amount of the second elongate element by the second drive part according to the rotation angle of the shaft in the first direction, and the controller is configured, when the shaft is rotated about the rotation axis of the shaft in a second direction, opposite to the first direction, which shortens the path lengths of the first elongate element and the second elongate element, to correct the rotation amounts of the first drive part and the second drive part so as to increase the winding amount of the first elongate element by the first drive part and the winding amount of the second elongate element by the second drive part according to the rotation angle of the shaft in the second direction.

18. The controller according to claim 12, wherein the first jaw member and the second jaw member forms a pair of scissors configured to cut an object, and the controller is configured:

when the opening angle between the first jaw member and the second jaw member is zero degree, which corresponds to a threshold, to set correction amounts of the rotation amounts of the first drive part and the second drive part to zero; and to increase absolute values of the correction amounts of the rotation amounts of the first drive part and the second drive part, as the operating angle deviates from the threshold and as the rotation angle of the shaft increases.

19. The controller according to claim 12, wherein the first jaw member and the second jaw member form a gripping type end effector configured to grip an object, and the controller is configured to correct, according to the rotation angle of the shaft about the rotation axis of the shaft, the rotation amounts of the first drive part and the second drive part.

20. A method of controlling a surgical system that comprises: a patient-side apparatus including an arm to which a surgical instrument is to be attached;

an operator-side apparatus including an operation part configured to receive an operation for operating the surgical instrument; and the controller configured to control an operation of the surgical instrument based on a command from the operation part, wherein the surgical instrument includes: a shaft; a first jaw member and a second jaw member provided on a side of a distal end of the shaft; a first elongate element for operating the first jaw member; and a second elongate element for operating the second jaw member, the arm includes a first drive part configured to drive the first elongate element and a second drive part configured to drive the second elongate element, and the controller is configured to control rotation amounts of the first drive part and the second drive part such that an opening angle between the first jaw member and the second jaw member corresponds to an operating angle received by the operation part for opening and closing the first jaw member and the second jaw member, the method comprising:

receiving, from the operation part, the operating angle for opening and closing the first jaw member and the second jaw member; and correcting, according to a rotation angle of the shaft about a rotation axis of the shaft, the rotation amounts of the first drive part and the second drive part that correspond to the operating angle.

\* \* \* \* \*